United States Patent
Luke et al.

(10) Patent No.: US 10,793,554 B2
(45) Date of Patent: Oct. 6, 2020

(54) SOLID FORMS OF 4-(2-FLUORO-4-(1-METHYL-1H-BENZO[D]IMIDAZOL-5-YL)BENZOYL)PIPERAZIN-1-YL)(1-HYDROXYCYCLOPROPYL)METHANONE

(71) Applicant: FORMA Therapeutics, Inc., Watertown, MA (US)

(72) Inventors: George P. Luke, Clinton, CT (US); Stephen Hubbs, Groton, CT (US); Matthew W. Martin, Arlington, MA (US); Robert Wenslow, Cream Ridge, NJ (US); Yawei Shi, Westfield, NJ (US); Jun Huang, San Diego, CA (US)

(73) Assignee: Forma Therapeutics, Inc., Watertown, MA (US)

( * ) Notice: Subject to any disclaimer, the term of this patent is extended or adjusted under 35 U.S.C. 154(b) by 0 days.

(21) Appl. No.: 16/667,602

(22) Filed: Oct. 29, 2019

(65) Prior Publication Data

US 2020/0131155 A1    Apr. 30, 2020

Related U.S. Application Data

(60) Provisional application No. 62/752,229, filed on Oct. 29, 2018.

(51) Int. Cl.
    *C07D 403/10* (2006.01)

(52) U.S. Cl.
    CPC ........ *C07D 403/10* (2013.01); *C07B 2200/13* (2013.01)

(58) Field of Classification Search
    CPC .................................................. C07D 403/10
    See application file for complete search history.

(56) References Cited

U.S. PATENT DOCUMENTS

| | | |
|---|---|---|
| 5,011,928 A | 4/1991 | Venero et al. |
| 5,510,345 A | 4/1996 | Tuba et al. |
| 5,759,837 A | 6/1998 | Kuhajda et al. |
| 5,856,326 A | 1/1999 | Anthony et al. |
| 6,080,860 A | 6/2000 | Karimian et al. |
| 6,410,540 B1 | 6/2002 | Goehring et al. |
| 6,469,046 B1 | 10/2002 | Daines et al. |
| 6,486,192 B1 | 11/2002 | Daines et al. |
| 6,486,211 B1 | 11/2002 | Daines et al. |
| 6,492,368 B1 | 12/2002 | Dorsch et al. |
| 6,498,187 B1 | 12/2002 | Christensen, IV et al. |
| 6,559,179 B1 | 5/2003 | Gaitanopoulos et al. |
| 6,608,059 B1 | 8/2003 | Daines et al. |
| 6,617,317 B1 | 9/2003 | Adams et al. |
| 6,670,388 B1 | 12/2003 | Daines et al. |
| 6,723,749 B2 | 4/2004 | Christensen et al. |
| 6,897,207 B2 | 5/2005 | Cox et al. |
| 7,309,714 B2 | 12/2007 | Duffy et al. |
| 7,375,134 B2 | 5/2008 | Bayly et al. |
| 7,459,448 B2 | 12/2008 | Blackburn et al. |
| 7,473,688 B2 | 1/2009 | Bergstrom et al. |
| 7,501,407 B2 | 3/2009 | Castelhano et al. |
| 7,504,400 B2 | 3/2009 | Meerpoel et al. |
| 7,511,062 B2 | 3/2009 | Kuang et al. |
| 7,601,716 B2 | 10/2009 | Dorsey et al. |
| 7,649,012 B2 | 1/2010 | Kuhajda et al. |
| 7,662,826 B2 | 2/2010 | Seno et al. |
| 7,671,219 B2 | 3/2010 | Shigemitsu et al. |
| 7,682,857 B2 | 3/2010 | Hanamaki et al. |
| 7,728,153 B2 | 6/2010 | Smith et al. |
| 7,763,623 B2 | 7/2010 | Palani et al. |
| 7,795,284 B2 | 9/2010 | Galcera-Contour et al. |
| 7,799,826 B2 | 9/2010 | Smith et al. |
| 7,807,676 B2 | 10/2010 | Wang et al. |
| 7,816,360 B2 | 10/2010 | Meerpoel et al. |
| 7,834,015 B2 | 11/2010 | Jones et al. |
| 7,919,502 B2 | 4/2011 | Dorsey et al. |
| 7,935,694 B2 | 5/2011 | Blackburn et al. |
| 7,943,616 B2 | 5/2011 | Cox et al. |
| 7,943,620 B2 | 5/2011 | Harbeson et al. |
| 7,973,037 B2 | 7/2011 | Bayly et al. |
| 7,977,374 B2 | 7/2011 | Ferrigno et al. |
| 7,998,995 B2 | 8/2011 | Boren et al. |
| 8,008,301 B2 | 8/2011 | Beavers et al. |
| 8,017,637 B2 | 9/2011 | Galcera-Contour et al. |
| 8,080,561 B2 | 12/2011 | Dorsey et al. |
| 8,088,923 B2 | 1/2012 | Romo et al. |
| 8,114,880 B2 | 2/2012 | Meerpoel et al. |
| 8,129,398 B2 | 3/2012 | Beaulieu et al. |
| 8,173,629 B2 | 5/2012 | Singh et al. |
| 8,188,084 B2 | 5/2012 | Jones et al. |
| 8,242,129 B2 | 8/2012 | Tsuhako et al. |
| 8,263,633 B2 | 9/2012 | Blaquiere et al. |
| 9,428,464 B2 | 8/2016 | Courtney et al. |
| 9,809,552 B2 | 11/2017 | Staehle et al. |
| 10,399,951 B2 | 9/2019 | Bair et al. |
| 10,450,286 B2 | 10/2019 | Bair et al. |

(Continued)

FOREIGN PATENT DOCUMENTS

| CA | 2260767 A1 | 1/1998 |
|---|---|---|
| CA | 2391534 A1 | 5/2001 |

(Continued)

OTHER PUBLICATIONS

Aicher, T.D., et al., Secondary Amides of ®-3,3,3-Trifluoro-2-hydroxy-2-methylpropionic Acid as Inhibitors of Pyruvate Dehydrogenase Kinase, J. Med. Chem., 43: 236-249 (2000).

(Continued)

*Primary Examiner* — Bruck Kifle
(74) *Attorney, Agent, or Firm* — Barnes & Thornburg LLP

(57) ABSTRACT

The present disclosure reports solid forms of (4-(2-fluoro-4-(1-methyl-1H- benzo[d]imidazol-5-yl)benzoyl)piperazin-1-yl)(1-hydroxycyclopropyl)methanone:

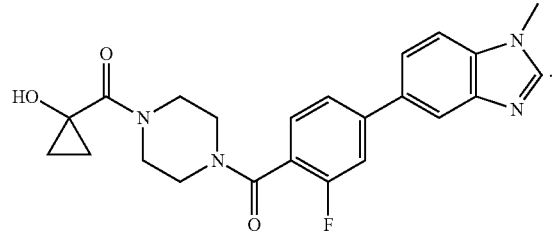

23 Claims, 15 Drawing Sheets

(56) References Cited

U.S. PATENT DOCUMENTS

| | | |
|---|---|---|
| 10,457,655 B2 | 10/2019 | Bair et al. |
| 10,472,342 B2 | 11/2019 | Bair et al. |
| 2002/0115671 A1 | 8/2002 | Goehring et al. |
| 2003/0138432 A1 | 7/2003 | Glazier |
| 2003/0170244 A1 | 9/2003 | Pluenneke et al. |
| 2003/0220392 A1 | 11/2003 | Leber et al. |
| 2004/0001801 A1 | 1/2004 | Madison et al. |
| 2004/0022779 A1 | 2/2004 | Rudel et al. |
| 2004/0024050 A1 | 2/2004 | Smith et al. |
| 2004/0053931 A1 | 3/2004 | Cox et al. |
| 2004/0058988 A1 | 3/2004 | Christensen, IV et al. |
| 2004/0082786 A1 | 4/2004 | Zhu et al. |
| 2004/0122033 A1 | 6/2004 | Nargund et al. |
| 2005/0043300 A1 | 2/2005 | Middleton et al. |
| 2005/0240023 A1 | 10/2005 | Bayly et al. |
| 2005/0261292 A1 | 11/2005 | Antel et al. |
| 2005/0267304 A1 | 12/2005 | Cox et al. |
| 2005/0288213 A1 | 12/2005 | MacNeil et al. |
| 2006/0040906 A1 | 2/2006 | Bakshi et al. |
| 2006/0100194 A1 | 5/2006 | Blackburn et al. |
| 2006/0106062 A1 | 5/2006 | Kuang et al. |
| 2006/0128963 A1 | 6/2006 | Sings et al. |
| 2006/0148721 A1 | 7/2006 | Erondu |
| 2006/0160834 A1 | 7/2006 | Fong et al. |
| 2006/0270650 A1 | 11/2006 | MacNeil et al. |
| 2007/0010513 A1 | 1/2007 | Aslanian et al. |
| 2007/0032529 A1 | 2/2007 | Takagi et al. |
| 2007/0099884 A1 | 5/2007 | Erondu et al. |
| 2007/0112000 A1 | 5/2007 | Barton et al. |
| 2007/0142394 A1 | 6/2007 | Solomon et al. |
| 2007/0161615 A1 | 7/2007 | Andrews et al. |
| 2007/0167435 A1 | 7/2007 | Mutahi et al. |
| 2007/0173495 A1 | 7/2007 | Palani et al. |
| 2007/0191383 A1 | 8/2007 | Meerpoel et al. |
| 2007/0203236 A1 | 8/2007 | Smith et al. |
| 2007/0208087 A1 | 9/2007 | Sanders et al. |
| 2007/0244186 A1 | 10/2007 | Galcera-Contour et al. |
| 2007/0249579 A1 | 10/2007 | Wang et al. |
| 2008/0032972 A1 | 2/2008 | Dorsey et al. |
| 2008/0064632 A1 | 3/2008 | Amatruda et al. |
| 2008/0139572 A1 | 6/2008 | Wang et al. |
| 2008/0166378 A1 | 7/2008 | Schimmer et al. |
| 2008/0188529 A1 | 8/2008 | Bayly et al. |
| 2008/0200376 A1 | 8/2008 | MacCoss et al. |
| 2008/0207569 A1 | 8/2008 | Spada |
| 2008/0207605 A1 | 8/2008 | Spada |
| 2008/0242677 A1 | 10/2008 | Dehmlow et al. |
| 2008/0269234 A1 | 10/2008 | Gandhi et al. |
| 2008/0312247 A1 | 12/2008 | Gant et al. |
| 2008/0318969 A1 | 12/2008 | Harbeson et al. |
| 2009/0048276 A1 | 2/2009 | Goulet et al. |
| 2009/0082560 A1 | 3/2009 | Kobayashi et al. |
| 2009/0105213 A1 | 4/2009 | Blackburn et al. |
| 2009/0105305 A1 | 4/2009 | Butlin et al. |
| 2009/0111789 A1 | 4/2009 | Bartkovitz et al. |
| 2009/0118332 A1 | 5/2009 | Butlin et al. |
| 2009/0156591 A1 | 6/2009 | Ferrigno et al. |
| 2009/0163545 A1 | 6/2009 | Goldfarb |
| 2009/0176765 A1 | 7/2009 | Jones et al. |
| 2009/0197863 A1 | 8/2009 | Chu et al. |
| 2009/0197894 A1 | 8/2009 | Fu et al. |
| 2009/0209523 A1 | 8/2009 | Jones et al. |
| 2009/0253677 A1 | 10/2009 | Beaulieu et al. |
| 2009/0264402 A1 | 10/2009 | Jaehne et al. |
| 2009/0264416 A1 | 10/2009 | Ho et al. |
| 2009/0275624 A1 | 11/2009 | Galcera-Contour et al. |
| 2009/0286778 A1 | 11/2009 | Combs et al. |
| 2009/0325877 A1 | 12/2009 | Grunt et al. |
| 2009/0325980 A1 | 12/2009 | Meerpoel et al. |
| 2010/0029621 A1 | 2/2010 | Cooke et al. |
| 2010/0048576 A1 | 2/2010 | Dorsey et al. |
| 2010/0069367 A1 | 3/2010 | Boren et al. |
| 2010/0125075 A1 | 5/2010 | Pratt et al. |
| 2010/0135954 A1 | 6/2010 | Tsuhako et al. |
| 2010/0160290 A1 | 6/2010 | Kobayashi et al. |
| 2010/0190856 A1 | 7/2010 | Colomer Bosch et al. |
| 2010/0305121 A1 | 12/2010 | Smith et al. |
| 2010/0317658 A1 | 12/2010 | Galcera-Contour et al. |
| 2011/0039820 A1 | 2/2011 | Blackburn et al. |
| 2011/0076291 A1 | 3/2011 | Blaquiere et al. |
| 2011/0105389 A1 | 5/2011 | Hoveyda et al. |
| 2011/0124021 A1 | 5/2011 | Medghalchi |
| 2011/0160204 A1 | 6/2011 | Dorsey et al. |
| 2011/0172230 A1 | 7/2011 | Ishii et al. |
| 2011/0230446 A1 | 9/2011 | Bayly et al. |
| 2011/0274654 A1 | 11/2011 | Bahadoor et al. |
| 2011/0274655 A1 | 11/2011 | Bahadoor et al. |
| 2012/0004260 A1 | 1/2012 | Ossovskaya et al. |
| 2012/0015958 A1 | 1/2012 | Cooke et al. |
| 2012/0021976 A1 | 1/2012 | Boyle et al. |
| 2012/0122842 A1 | 5/2012 | Curtin et al. |
| 2012/0149683 A1 | 6/2012 | Cox et al. |
| 2012/0156138 A1 | 6/2012 | Smith |
| 2012/0178739 A1 | 7/2012 | Blackburn et al. |
| 2012/0195961 A1 | 8/2012 | Kritikou et al. |
| 2012/0196851 A1 | 8/2012 | Varrone et al. |
| 2012/0208827 A1 | 8/2012 | Dock et al. |
| 2012/0264737 A1 | 10/2012 | Oslob et al. |
| 2014/0329795 A1 | 11/2014 | Courtney et al. |
| 2015/0051211 A1 | 2/2015 | Ji et al. |
| 2016/0002188 A1* | 1/2016 | Bair ............... A61K 31/4985 424/85.7 |
| 2017/0312273 A1* | 11/2017 | Millan ............. A61K 31/496 |
| 2018/0050997 A1 | 2/2018 | Bair et al. |
| 2018/0370933 A1 | 12/2018 | Bair et al. |
| 2019/0241532 A1 | 8/2019 | Bair et al. |
| 2019/0241533 A1 | 8/2019 | Bair et al. |
| 2020/0017458 A1 | 1/2020 | Bair et al. |

FOREIGN PATENT DOCUMENTS

| | | |
|---|---|---|
| CA | 2447023 A1 | 11/2002 |
| CA | 2492225 A1 | 1/2004 |
| CA | 2609957 A1 | 1/2007 |
| CA | 2634250 A1 | 7/2007 |
| CA | 2634847 A1 | 7/2007 |
| CA | 2637717 A1 | 8/2007 |
| CA | 2668094 A1 | 5/2008 |
| CA | 2696053 A1 | 9/2008 |
| CA | 2759098 A1 | 10/2010 |
| CA | 2764526 A1 | 12/2010 |
| CA | 2778990 A1 | 5/2011 |
| CN | 1272107 A | 3/2000 |
| CN | 101203510 A | 6/2008 |
| CN | 101384553 A | 3/2009 |
| CN | 101400682 A | 4/2009 |
| CN | 101426777 A | 5/2009 |
| CN | 101668520 A | 3/2010 |
| CN | 102372698 A | 3/2012 |
| CN | 102627610 A | 8/2012 |
| CN | 103420890 A | 12/2013 |
| EP | 0922099 A1 | 6/1999 |
| EP | 1073891 A2 | 2/2001 |
| EP | 1164374 A1 | 12/2001 |
| EP | 1255567 A1 | 11/2002 |
| EP | 1290446 A2 | 3/2003 |
| EP | 1397360 A1 | 3/2004 |
| EP | 1401469 A2 | 3/2004 |
| EP | 1465631 A2 | 10/2004 |
| EP | 1482924 B1 | 12/2004 |
| EP | 1534074 A2 | 6/2005 |
| EP | 1545572 A2 | 6/2005 |
| EP | 1751131 A1 | 2/2007 |
| EP | 1764616 A2 | 3/2007 |
| EP | 1807102 A2 | 7/2007 |
| EP | 1814879 A1 | 8/2007 |
| EP | 1831209 A2 | 9/2007 |
| EP | 1884513 A1 | 2/2008 |
| EP | 1896453 A1 | 3/2008 |
| EP | 1926721 A2 | 6/2008 |
| EP | 1966143 A2 | 9/2008 |
| EP | 1976848 A2 | 10/2008 |
| EP | 1976854 A2 | 10/2008 |
| EP | 1981341 A2 | 10/2008 |

(56) References Cited

FOREIGN PATENT DOCUMENTS

| | | |
|---|---|---|
| EP | 2019091 A1 | 1/2009 |
| EP | 2074103 A1 | 7/2009 |
| EP | 2076494 A1 | 7/2009 |
| EP | 2091951 A2 | 8/2009 |
| EP | 2139877 A1 | 1/2010 |
| EP | 2142533 A1 | 1/2010 |
| EP | 2144604 A2 | 1/2010 |
| EP | 2170802 A1 | 4/2010 |
| EP | 2233486 A1 | 9/2010 |
| EP | 2274288 A2 | 1/2011 |
| EP | 2445506 A1 | 5/2012 |
| EP | 2483277 A1 | 8/2012 |
| EP | 2485728 A1 | 8/2012 |
| EP | 2493310 A1 | 9/2012 |
| EP | 2493910 A1 | 9/2012 |
| EP | 2503890 A1 | 10/2012 |
| FR | 2829766 A1 | 3/2003 |
| KR | 100637955 A1 | 10/2006 |
| KR | 20080080201 A | 9/2008 |
| KR | 20080087833 A | 10/2008 |
| KR | 20080091814 A | 10/2008 |
| RU | 2194044 C2 | 12/2002 |
| RU | 2011/108493 A | 3/2011 |
| WO | WO 1994/002466 A1 | 2/1994 |
| WO | WO 1996/030343 A1 | 10/1996 |
| WO | WO 1998/003648 A1 | 1/1998 |
| WO | WO 1999/016751 A1 | 4/1999 |
| WO | WO 1999/054728 A2 | 10/1999 |
| WO | WO 1999/064446 A1 | 12/1999 |
| WO | WO 2000/022909 A2 | 4/2000 |
| WO | WO 2000/078309 A1 | 12/2000 |
| WO | WO 2000/078310 A1 | 12/2000 |
| WO | WO 2001/014362 A1 | 3/2001 |
| WO | WO 2001/014363 A1 | 3/2001 |
| WO | WO 2001/014364 A1 | 3/2001 |
| WO | WO 2001/017942 A1 | 3/2001 |
| WO | WO 2001/030752 A2 | 5/2001 |
| WO | WO 2001/030775 A1 | 5/2001 |
| WO | WO 2001/036003 A2 | 5/2001 |
| WO | WO 2001/090099 A1 | 11/2001 |
| WO | WO 2001/096873 A2 | 12/2001 |
| WO | WO 2002/000620 A1 | 1/2002 |
| WO | WO 2002/000646 A1 | 1/2002 |
| WO | WO 2002/002119 A1 | 1/2002 |
| WO | WO 2002/009651 A2 | 2/2002 |
| WO | WO 2002/009688 A1 | 2/2002 |
| WO | WO 2002/024197 A1 | 3/2002 |
| WO | WO 2002/026745 A1 | 4/2002 |
| WO | WO 2002/055661 A2 | 7/2002 |
| WO | WO 2002/080952 A2 | 10/2002 |
| WO | WO 2002/095007 A2 | 11/2002 |
| WO | WO 2003/000688 A1 | 1/2003 |
| WO | WO 2003/024956 A1 | 3/2003 |
| WO | WO 2004/009015 A2 | 1/2004 |
| WO | WO 2004/014370 A2 | 2/2004 |
| WO | WO 2004/030637 A2 | 4/2004 |
| WO | WO 2004/037800 A1 | 5/2004 |
| WO | WO 2004/050022 A2 | 6/2004 |
| WO | WO 2004/110368 A2 | 12/2004 |
| WO | WO 2004/110375 A2 | 12/2004 |
| WO | WO 2005/000217 A2 | 1/2005 |
| WO | WO 2005/009950 A2 | 2/2005 |
| WO | WO 2005/016344 A1 | 2/2005 |
| WO | WO 2005/035534 A1 | 4/2005 |
| WO | WO 2005/046685 A1 | 5/2005 |
| WO | WO 2005/073186 A1 | 8/2005 |
| WO | WO 2005/085226 A1 | 9/2005 |
| WO | WO 2005/097740 A1 | 10/2005 |
| WO | WO 2005/097746 A2 | 10/2005 |
| WO | WO 2005/097750 A1 | 10/2005 |
| WO | WO 2005/110413 A2 | 11/2005 |
| WO | WO 2005/116006 A1 | 12/2005 |
| WO | WO 2005/116009 A1 | 12/2005 |
| WO | WO 2006/021801 A1 | 3/2006 |
| WO | WO 2006/032322 A1 | 3/2006 |
| WO | WO 2006/034341 A2 | 3/2006 |
| WO | WO 2006/049933 A2 | 5/2006 |
| WO | WO 2006/051202 A1 | 5/2006 |
| WO | WO 2006/060461 A1 | 6/2006 |
| WO | WO 2006/067311 A2 | 6/2006 |
| WO | WO 2007/002057 A1 | 1/2007 |
| WO | WO 2007/029035 A2 | 3/2007 |
| WO | WO 2007/033175 A1 | 3/2007 |
| WO | WO 2007/038669 A2 | 4/2007 |
| WO | WO 2007/049532 A1 | 5/2007 |
| WO | WO 2007/068620 A1 | 6/2007 |
| WO | WO 2007/068641 A1 | 6/2007 |
| WO | WO 2007/075629 A2 | 7/2007 |
| WO | WO 2007/075688 A2 | 7/2007 |
| WO | WO 2007/080140 A1 | 7/2007 |
| WO | WO 2007/082840 A1 | 7/2007 |
| WO | WO 2007/087204 A2 | 8/2007 |
| WO | WO 2007/089634 A2 | 8/2007 |
| WO | WO 2007/092065 A2 | 8/2007 |
| WO | WO 2007/130468 A2 | 11/2007 |
| WO | WO 2007/137955 A1 | 12/2007 |
| WO | WO 2007/138351 A2 | 12/2007 |
| WO | WO 2007/138355 A1 | 12/2007 |
| WO | WO 2008/011453 A2 | 1/2008 |
| WO | WO 2008/030891 A2 | 3/2008 |
| WO | WO 2008/052658 A1 | 5/2008 |
| WO | WO 2008/059214 A1 | 5/2008 |
| WO | WO 2008/061399 A1 | 5/2008 |
| WO | WO 2008/066789 A2 | 6/2008 |
| WO | WO 2008/073825 A1 | 6/2008 |
| WO | WO 2008/075064 A1 | 6/2008 |
| WO | WO 2008/075070 A1 | 6/2008 |
| WO | WO 2008/075077 A1 | 6/2008 |
| WO | WO 2008/099000 A2 | 8/2008 |
| WO | WO 2008/106166 A2 | 9/2008 |
| WO | WO 2008/106167 A1 | 9/2008 |
| WO | WO 2008/109175 A1 | 9/2008 |
| WO | WO 2008/133273 A1 | 11/2008 |
| WO | WO 2008/133955 A1 | 11/2008 |
| WO | WO 2008/157751 A2 | 12/2008 |
| WO | WO 2009/000864 A1 | 12/2008 |
| WO | WO 2009/004356 A1 | 1/2009 |
| WO | WO 2009/064927 A2 | 5/2009 |
| WO | WO 2009/098282 A1 | 8/2009 |
| WO | WO 2009/099736 A2 | 8/2009 |
| WO | WO 2009/132202 A2 | 10/2009 |
| WO | WO 2009/143404 A1 | 11/2009 |
| WO | WO 2009/151910 A2 | 12/2009 |
| WO | WO 2010/017055 A2 | 2/2010 |
| WO | WO 2010/056309 A2 | 5/2010 |
| WO | WO 2010/120262 A1 | 10/2010 |
| WO | WO 2010/138589 A1 | 12/2010 |
| WO | WO 2010/150100 A1 | 12/2010 |
| WO | WO 2011/035018 A2 | 3/2011 |
| WO | WO 2011/036284 A1 | 3/2011 |
| WO | WO 2011/042145 A1 | 4/2011 |
| WO | WO 2011/053821 A1 | 5/2011 |
| WO | WO 2011/056635 A1 | 5/2011 |
| WO | WO 2011/066211 A1 | 6/2011 |
| WO | WO 2011/103546 A1 | 8/2011 |
| WO | WO 2011/140190 A1 | 11/2011 |
| WO | WO 2011/140296 A1 | 11/2011 |
| WO | WO 2011/163612 A1 | 12/2011 |
| WO | WO 2011/163619 A1 | 12/2011 |
| WO | WO 2012/016217 A1 | 2/2012 |
| WO | WO 2012/019430 A1 | 2/2012 |
| WO | WO 2012/037298 A1 | 3/2012 |
| WO | WO 2012/037299 A2 | 3/2012 |
| WO | WO 2012/064632 A1 | 5/2012 |
| WO | WO 2012/064642 A1 | 5/2012 |
| WO | WO 2012/071562 A2 | 5/2012 |
| WO | WO 2012/092442 A1 | 7/2012 |
| WO | WO 2012/096928 A2 | 7/2012 |
| WO | WO 2012/101013 A1 | 8/2012 |
| WO | WO 2012/122391 A1 | 9/2012 |
| WO | WO 2012/125521 A1 | 9/2012 |
| WO | WO 2012/130166 A1 | 10/2012 |
| WO | WO 2012/151451 A1 | 11/2012 |
| WO | WO 2012/151452 A1 | 11/2012 |

(56) References Cited

FOREIGN PATENT DOCUMENTS

| WO | WO 2013/028445 A1 | 2/2013 |
|---|---|---|
| WO | WO 2013/028495 A1 | 2/2013 |
| WO | WO 2013/033068 A1 | 3/2013 |
| WO | WO 2013/045413 A1 | 4/2013 |
| WO | WO 2013/060636 A1 | 5/2013 |
| WO | WO 2013/064083 A1 | 5/2013 |
| WO | WO 2013/078771 A1 | 6/2013 |
| WO | WO 2013/156608 A1 | 10/2013 |
| WO | WO 2014/044356 A1 | 3/2014 |
| WO | WO 2014/146747 A1 | 9/2014 |
| WO | WO 2014/164749 A1 | 10/2014 |
| WO | WO 2014/164767 A1 | 10/2014 |
| WO | WO 2015/014446 A1 | 2/2015 |
| WO | WO 2016/205590 A1 | 12/2016 |
| WO | WO 2016/205633 A1 | 12/2016 |
| WO | WO 2017/189613 A1 | 11/2017 |

OTHER PUBLICATIONS

Berod, Luciana, et al., "*De novo* fatty acid synthesis controls the fate between regulatory T and T helper 17 cells," Nature Medicine, vol. 20, No. 11, Nov. 2014. 1327-1335.

Clayden, Greeves, Warren and Wothers, Summary: The Three Major Approaches to the Synthesis of Aromatic Heterocycles, Aromatic heterocycles 2: synthesis, Organic Chemistry, Oxford University Press, 44: 1214-1215 (2001).

Database Registry [Online] Chemical Abstracts Service, Columbus, Ohio, US; Database accession No. 1387900-07-3 (Aug. 8, 2012); Database accession No. 1014245-05-6 (Apr. 13, 2008); and, Database accession No. 927570-20-5 (Mar. 20, 2007). 1 page.

Database Registry [Online] Chemical Abstracts Service, Columbus, Ohio, US; Database accession No. 1630806-71-1 (Oct. 29, 2014); Database accession No. 1630806-69-7 (Oct. 29, 2014); Database accession No. 1630806-63-1 (Oct. 29, 2014); Database accession No. 1630806-59-5 (Oct. 29, 2014); Database accession No. 1630806-56-2 (Oct. 29, 2014); Database accession No. 1630806-55-1 (Oct. 29, 2014); Database accession No. 1630806-49-3 (Oct. 29, 2014); Database accession No. 1630806-44-8 (Oct. 29, 2014); Database accession No. 1630806-41-5 (Oct. 29, 2014); Database accession No. 871002-005-0 (Jan. 3, 2006).

De Schrijver, et al., RNA Interference-mediated Silencing of the Fatty Acid Synthase Gene Attenuates Growth and induces Morphological Changes and Apoptosis of LNCaP Prostate Cancer Cells, Cancer Res (2003) 63:3799-3804.

Endo, Yusuke, et al., "Obesity Drives Th17 Cell Differentiation by Inducing the lipid Metabolic Kinase, ACC1," Cell Reports, 12, Aug. 11, 2015, 1042-1055.

Fako, V.E., et al., Mechanism of Orlistat Hydrolysis by the Thioesterase of Human Fatty Acid Synthase, ACS Catal, 4: 3444-3453 (2014).

Fatima, S., et al., Molecular docking and 3D-QSAR studies on inhibitors of DNA damage signaling enzyme human PARP-1, Journal of Receptors and Signal Transduction, 32(4): 214-224 (2012).

Ferrigno, F., et al., Development of substituted 6-[4-fluoro-3-(piperazin-1-ylcarbonyl)benzyl]-4,5-dimethylpyridazin-3(2H)-ones as potent poly(ADP-ribose) polymerase-1 (PARP-1) inhibitors active in BRCA deficient cells, Bioorganic & Medicinal Chemistry Letters, 20(3): 1100-1105 (2010).

First Formal Official Action: Colombian Patent Application No. 15-242.983, dated Dec. 17, 2015.

First Formal Official Action: Cuban Patent Application No. 2015-0120, dated Dec. 3, 2015.

Flavin, R., et al., Fatty acid synthase as a potential therapeutic target in cancer, Future Oncol, 6(4): 551-562 (2010).

Gansler TS, et al., Increased expression of fatty acid synthase {OA-519} in ovarian neoplasms predicts shorter survival. Hum. Pathol. (1997) 28 (6): 686-92.

Heaton, et al., Dengue virus nonstructural protein 3 redistributes fatty acid synthase to sites of viral replication and increases cellular fatty acid synthesis. Proc. Natl. Acad. Sci., (210) 107(40): 17345-17350.

Harriman, Geraldine, et al., "Acetyl-CoA carboxylase inhibition by ND-630 reduces hepatic steatosis, improves insulin sensitivity, and modulates dyslipidemia in rats," PNAS Early Edition, 1-10.

Harrison, Stephen a., et al., "Orlistat in the Treatment of NASH: A Case Series," the American Journal of Gastroenterology, vol. 98, No. 4, 2003, 926-930.

Harrison, S.A., et al., "A pilot study of orlistat treatment in obese, non-alchoholic steatohepatitis patients," Aliment Pharmacol Ther, 2004, 20, 623-628.

Hunt DA, et al., Mrna stability and overexpression of fatty acid synthase inhuman breast cancer cell lines. Anticancer Res. (2007) 27{1A): 27-34.

International Search Report for PCT/US2014/023388, 4 pages (dated Aug. 18, 2014).

International Search Report for PCT/US2017/029469, 4 pages (dated Jun. 24, 2017).

International Search Report for PCT/US2019/058601, 9 pages (dated Jan. 16, 2020).

Jones, S.F. And Infante, J.R., Molecular Pathways: Fatty Acid Synthase, Clin Cancer Res; 21(24): 5434-5438 (2015).

Kant, Shiva, et al., "Myelopoietic Efficacy of Orlistat in Murine Hosts Bearing T Cell Lymphoma: Implication in Macrophage Differentiation and Activation," PLOS One, Dec. 2013, vol. 8, Issue 12, e82396, 1-14.

Kridel, et al., Orlistat Is a Novel Inhibitor of Fatty Acid Synthase with Antitumor Activity, Cancer Res (2004) 54:2070-2075.

Kuhajda FP, Fatty acid synthase an dcancer: New application of an old pathway. Cancer Research, (2006) 66(12):5977-5980.

Li, et al., Fatty acid synthase expression is induced by the Epstein-Barr virus immediate-early protein BRLF1 and is required for lytic viral gene expression. Journal of Virology, (2004) 78(8):4197-4206.

Martin, Matthew W., et al., "Discovery and optimization of novel piperazines as potent inhibitors of fatty acid synthase (FASN)," Bioorganic & Medicinal Chemistry Letters, 29, 2019, 1001-1006.

Menear, K.A., et al., 443-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1, Journal of Medicinal Chemistry, 51(20), 6581-6591 (2008).

Menendez JA and Lupu R, Fatty acid synthase and the lipogenic phenotype in cancer pathogenesis, Nature Review Cancer, (2007) 7: 763-777.

Montgomery, J.I., et al., Discovery and SAR of benzyl phenyl ethers as inhibitors of bacterial phenylalanyl-tRNA synthetase, Bioorganic & Medicinal Chemistry Letters, 19(3): 665-669 (2009).

Munger, et al., Systems-level metabolic flux profiling identifies fatty acid synthesis as a target for antiviral therapy. Nature Biotechnology, (2008) 26: 1179-1186.

Notice of First Formal Official Action: Panama Patent Application No. P1/2015/90868-01, dated Dec. 21, 2015.

Oliveras, et al., Novel anti-fatty acid synthase compounds with anti-cancer activity in HER2+breast cancer, Ann. N. Acad. Sci. (2010) 1210: 86-93.

Rassmann, et al., The human fatty acid synthase: a new therapeutic target for coxsackievirus B3-induced diseases? Antiviral Research, (2007) 76: 150-158.

Rhee, H-K., et al., Synthesis and cytotoxicity of 2-phenylquinazolin-4(3)-one derivatives, European Journal of Medicinal Chemistry, 46(9): 3900-3908 (2011).

Samsa, et al., Dengue virus capsid protein usurps lipid droplets for viral particle formation. PLoS Pathegens, (2009) 5 10):e1000632.

Smagris, Eriks, "Pnpla3l148M Knockin Mice Accumulate PNPLA3 on Lipid Droplets and Develp Hepatic Steatosis," Hepatology, vol. 61, No. 1, 2015, 108-118.

Vazquez, et al., Discovery of GSK837149A, an inhibitor of human fatty acid synthase targeting the b-ketoacyl reductase reaction, FEBS Journal (20008) 275:1556-1567.

Written Opinion for PCT/US17/29469 from the International Searching Authority dated Oct. 2, 2017.

Xenical_Orlistat_Prescribing_Infomation insert. Genentech, 2015, Reference ID: 3803457.

Yang, W., et al, Fatty acid synthase is up-regulated during hepatitis C virus infection and regulates hepatitis C virus entry and production. Hepatology (2008) 48, 13967-1403.

(56) References Cited

OTHER PUBLICATIONS

Zhang, et al., b-Lactam congeners of orlistat as inhibitors of fatty acid synthase, Bioorg. Med. Chem. Let. 18 491-2494 (2008).

* cited by examiner

SOLID FORMS OF 4-(2-FLUORO-4-(1-METHYL-1H-BENZO[D]IMIDAZOL-5-YL)BENZOYL)PIPERAZIN-1-YL)(1-HYDROXYCYCLOPROPYL)METHANONE

CROSS-REFERENCE TO RELATED APPLICTIONS

This application claims the benefit of U.S. Provisional Application No. 62/752,229, filed Oct. 29, 2018, which is incorporated by reference in its entirety.

TECHNICAL FIELD

The present disclosure relates to pharmaceutical compositions, including solid forms of a certain compound useful for inhibiting fatty acid synthase (FASN).

BACKGROUND

Chemical compounds can form one or more different pharmaceutically acceptable solid forms, such as various polymorph crystal forms. Individual solid forms of bioactive chemical compounds can have different properties. There is a need for the identification and selection of appropriate solid forms of bioactive chemical compounds (including appropriate crystalline forms, where applicable) for the development of pharmaceutically acceptable dosage forms for the treatment of various diseases or conditions.

The compound, (4-(2-fluoro-4-(1-methyl-1H-benzo[d]imidazol-5-yl)benzoyl)piperazin-1-yl)(1-hydroxycyclopropyl)methanone (Compound 1), is a small molecule inhibitor of fatty acid synthase (FASN):

Compound 1

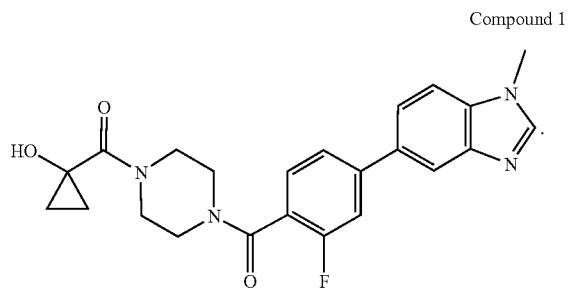 [SMILES: Cn1cnc2cc(-c3ccc(C(=O)N4CCN(C(=O)C5(O)CC5)CC4)c(F)c3)ccc21]

Compound 1 is disclosed in PCT Application Publication No. WO 2014/164749 as one of many compounds suitable as small molecule inhibitors of FASN.

Therapeutic compounds often exist in a variety of solid forms having different properties. There remains a need for identifying solid forms of Compound 1 useful for various therapeutic applications.

SUMMARY

Novel solid forms of Compound 1 disclosed herein include Form B, Form C, and Form X, as well as compositions comprising a solid form of Compound 1 comprising one or more of Form B, Form C, Form X and Form Z. In addition, a novel mixture of solid forms of Compound 1, Mixture A, is disclosed herein, as well as compositions comprising Mixture A.

A novel Compound 1 Mixture A can be identified by X-ray Powder Diffraction (XRPD), having one or more characteristic diffractions at angles (2 theta±0.2) of 9.6, 10.1, 15.4, 19.6, and 22.3. A novel Compound 1 Mixture A can be identified by XRPD having characteristic diffractions at angles (2 theta±0.2) of 9.6, 10.1, 15.4, 19.6, and 22.3, and not having a characteristic diffraction at angle (2 theta±0.2) of 24.2. A novel Compound 1 Mixture A can be identified (i) by differential scanning calorimetry (DSC) having two endotherms at 226.2° C. and 229.1° C.; and (ii) by XRPD having one or more characteristic diffractions at angles (2 theta±0.2) of 9.6, 10.1, 15.4, 19.6, and 22.3.

A novel Compound 1 Form B can be identified by XRPD, having one or more characteristic diffractions at angles (2 theta±0.2) of 9.6, 10.1, 15.4, 19.6, and 22.3. A novel Compound 1 Form B can be identified by XRPD, having one or more characteristic diffractions at angles (2 theta±0.2) of 9.6, 10.1, 15.4, 19.6, and 22.3, and not having one or more characteristic diffractions at angles (2 theta±0.2) of 7.2, 8.4, 14.9, 16.1, and 17.8 and/or not having a characteristic diffraction at angle (2 theta±0.2) of 24.2. A novel Compound 1 Form B can be identified (i) by DSC having one endotherm at 225.7° C.; and (ii) by XRPD having one or more characteristic diffractions at angles (2 theta±0.2) of 9.6, 10.1, 15.4, 19.6, and 22.3.

A novel Compound 1 Form C can be identified by XRPD, having one or more characteristic diffractions at angles (2 theta±0.2) of 9.6, 10.1, 15.4, 19.6, 22.2, and 26.6.

A novel Compound 1 Form X can be identified by XRPD, having one or more characteristic diffractions at angles (2 theta±0.2) of 7.2, 8.4, 14.9, 16.1, and 17.8.

A novel Compound Form Z can be identified by XRPD, having characteristic diffraction at angles (2 theta) as exemplified in FIG. 11.

The Applicant has also discovered that novel Compound 1 solid forms or solid form mixtures (e.g., Form B, Form C, Form X, and Mixture A) can also be obtained by subjecting or maintaining a Compound 1 solid form under physical conditions effective to convert Compound 1 as a first solid form into Compound 1 as a second solid form.

DETAILED DESCRIPTION

Figure 1:
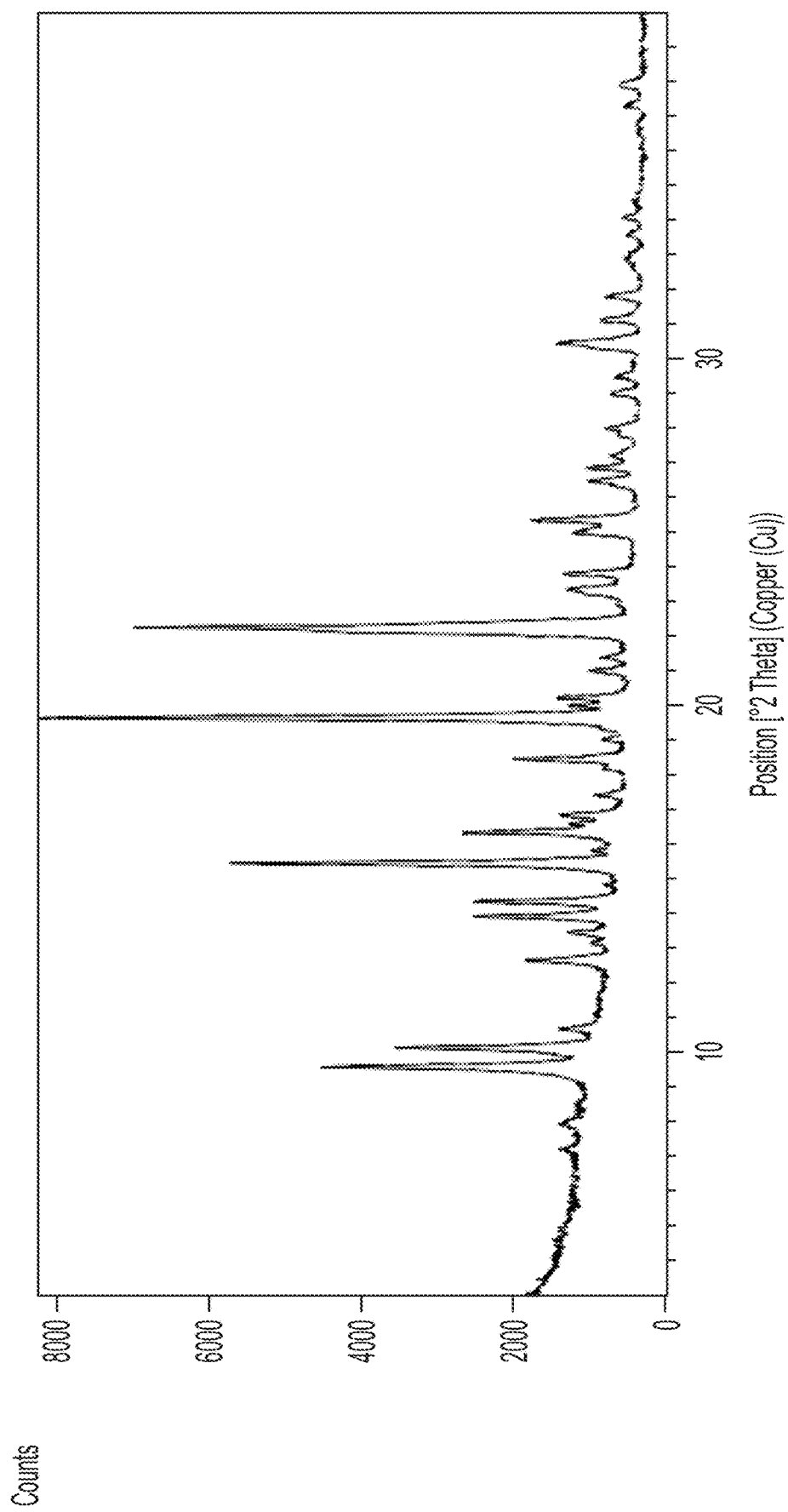
FIG. 1 depicts an XRPD pattern of Compound 1 Mixture A.

The present disclosure provides novel Compound 1 solid forms and mixtures thereof, pharmaceutical compositions thereof, methods of preparation thereof, and methods of use thereof. Compound 1 is the FASN inhibitor bioactive compound (4-(2-fluoro-4-(1-methyl-1H-benzo [d]imidazol-5-yl)benzoyl)piperazin-1-yl)(1-hydroxycyclopropyl)methanone (Compound 1), can be prepared as one or more solid forms. The chemical structure of Compound 1 is shown below:

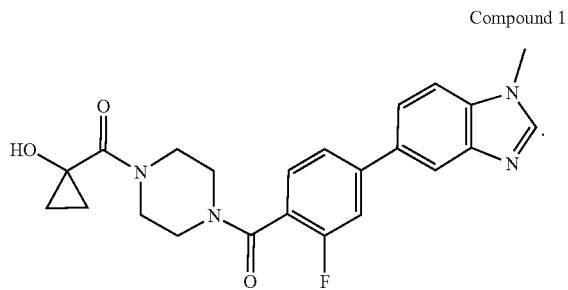 [SMILES: Cn1cnc2cc(-c3ccc(C(=O)N4CCN(C(=O)C5(O)CC5)CC4)c(F)c3)ccc21]

Compound 1

Compound 1 can occur in an amorphous solid form or in a crystalline solid form or in mixtures of solid forms. Crystalline solid forms of Compound 1 can exist in one or more unique solid forms, which can additionally comprise one or more equivalents of water or solvent (i.e., hydrates or solvates, respectively). Accordingly, in some embodiments, the present disclosure provides a crystalline solid form of Compound 1. Crystalline forms of Compound 1 disclosed herein have distinct characteristics (e.g., characteristic XRPD peaks disclosed herein).

Novel Compound 1 solid forms or solid form mixtures can be obtained by methods reported in the Examples (e.g., Example 2). Different methods of preparation can lead to different solid forms or solid form mixtures. For example, Compound 1 Form B can be obtained from a slurry comprising Compound 1 in ethanol at 50° C., as described in Example 2.

In some embodiments, certain solid forms or solid form mixtures of Compound 1 can be converted from one solid form to another solid form. For example, subjecting Compound 1 Mixture A and/or Form C to certain conditions yields at least Form B. Conditions suitable for converting Mixture A and/or Form C to Form B include conditions such as slurrying at room temperature, slurrying at 50° C., slurrying at 80° C., slurrying at reflux, and recrystallization.

Certain solid forms or solid form mixtures of Compound 1 can be prepared by forming a suspension (i.e., "slurrying") comprising Compound 1 Mixture A and/or Form C and a solvent, and maintaining the suspension for a period of time sufficient to generate certain solid forms of Compound 1 (e.g., Form B). Exemplary solvents suitable to generate Form B include ethyl acetate (EtOAc), acetonitrile (ACN), heptane, isopropyl alcohol (IPA), and ethanol (EtOH). In some embodiments, a solvent is EtOAc. In some embodiments, a solvent is ACN. In some embodiments, a solvent is heptane. In some embodiments, a solvent is IPA. In some embodiments, a solvent is EtOH. In some embodiments, the suspension is maintained at room temperature. In some embodiments, the suspension is heated to a temperature between about 40° C. and 110° C. In some embodiments, the suspension is heated to a temperature of about 50° C. In some embodiments, the suspension is heated to a temperature of about 80° C. In some embodiments, the suspension is heated to a temperature of about 100° C. In some embodiments, the suspension is heated to reflux.

Certain solid forms or solid form mixtures of Compound 1 can be prepared by forming a suspension (i.e., "slurrying") comprising Compound 1 Mixture A, Form C, and/or Form X and a solvent, and maintaining the suspension for a period of time sufficient to generate certain solid forms of Compound 1 (e.g., Form B). Exemplary solvents suitable to generate Form B include ethyl acetate (EtOAc), acetonitrile (ACN), heptane, isopropyl alcohol (IPA), and ethanol (EtOH). In some embodiments, a solvent is EtOAc. In some embodiments, a solvent is ACN. In some embodiments, a solvent is heptane. In some embodiments, a solvent is IPA. In some embodiments, a solvent is EtOH. In some embodiments, the suspension is maintained at room temperature. In some embodiments, the suspension is heated to a temperature between about 40° C. and 110° C. In some embodiments, the suspension is heated to a temperature of about 50° C. In some embodiments, the suspension is heated to a temperature of about 80° C. In some embodiments, the suspension is heated to a temperature of about 100° C. In some embodiments, the suspension is heated to reflux. In some embodiments, the disclosure relates to a solid form of Compound 1 that would be obtained by the foregoing process (or any embodiment thereof). In such embodiments, the solid form need not be prepared by such process, so long as the solid form is the same as the solid form that would be obtained by such process.

In some embodiments, certain solid forms of Compound 1 can be prepared by forming a salt of Compound 1, neutralizing said salt of Compound 1, and then allowing certain solid forms of Compound 1 (e.g., Form X) to precipitate from solution. For example, protonation of Compound 1 Form B with HCl in acetonitrile, followed by neutralization with NaOH (aq), and allowing precipitation at room temperature generates Compound 1 Form X.

In some embodiments, a solid form mixture of Compound 1 (e.g., Mixture A) is a mixture of two solid forms (e.g., Form B and another solid form). In some embodiments, a solid form mixture of Compound 1 (e.g., Mixture A) comprises two solid forms (e.g., Form B and another solid form).

The solid forms of Compound 1 disclosed herein include Compound 1 Form B, Form C, and Form X, as well as compositions comprising a solid form of Compound 1 comprising one or more of Form B, Form C, and Form X. The solid form mixtures of Compound 1 disclosed herein include Compound 1 in Mixture A, as well as compositions comprising a solid form mixture of Compound 1, comprising Mixture A. The solid forms and solid form mixtures of Compound 1 can be identified by various analytical techniques, such as XRPD and DSC.

A novel Compound 1 Mixture A can be identified by XRPD, having one or more characteristic diffractions at angles (2 theta±0.2) of 9.6, 10.1, 15.4, 19.6, and 22.3. A novel Compound 1 Mixture A can be identified by XRPD having characteristic diffractions at angles (2 theta±0.2) of 9.6, 10.1, 15.4, 19.6, and 22.3, and not having a diffraction at angle (2 theta±0.2) of 24.2. In some embodiments, Compound 1 Mixture A can be identified by XRPD, having one or more characteristic diffractions at angles (2 theta±0.2) of 9.6, 10.1, 15.4, 19.6, 21.0, and 22.3. In some embodiments, Compound 1 Mixture A can be identified by XRPD, having one or more characteristic diffractions at angles (2 theta±0.2) of 9.6, 10.1, 15.4, 19.6, and 22.3, corresponding to d-spacing (angstroms±0.2) of 9.3, 8.7, 5.7, 4.5, and 4.0, respectively.

In some embodiments, Compound 1 Mixture A is characterized by an XPRD having one or more peaks at substantially the same angles (2 theta±0.2) of:

| |
|---|
| 7.9 |
| 9.6 |
| 10.1 |
| 10.7 |
| 12.6 |
| 13.4 |
| 13.9 |
| 14.3 |
| 15.4 |
| 16.3 |
| 16.8 |
| 17.4 |
| 18.5 |
| 19.6 |
| 20.2 |
| 21.0 |
| 21.4 |
| 22.1 |
| 22.2 |
| 23.4 |
| 23.8 |
| 25.0 |
| 25.3 |
| 26.5 |
| 26.8 |
| 27.2 |
| 28.0 |
| 29.0 |
| 29.4 |
| 30.5 |
| 31.1 |
| 31.8 |
| 32.9 |
| 33.6 |
| 34.1 |
| 37.3 |
| 37.9. |

In some embodiments, Compound 1 Mixture A is characterized by an XRPD having one or more peaks at substantially the same angles (2 theta±0.2), corresponding to d-spacing (angstroms±0.2L) of:

| 2 Theta | d-spacing (Å) |
|---|---|
| 7.9 | 11.1 |
| 9.6 | 9.3 |
| 10.1 | 8.7 |
| 10.7 | 8.3 |
| 12.6 | 7.0 |
| 13.4 | 6.6 |
| 13.9 | 6.4 |
| 14.3 | 6.2 |
| 15.4 | 5.7 |
| 16.3 | 5.4 |
| 16.8 | 5.3 |
| 17.4 | 5.1 |
| 18.5 | 4.8 |
| 19.6 | 4.5 |
| 20.2 | 4.4 |
| 21.0 | 4.2 |
| 21.4 | 4.2 |
| 22.1 | 4.0 |
| 22.2 | 4.0 |
| 23.4 | 3.8 |
| 23.8 | 3.7 |
| 25.0 | 3.6 |
| 25.3 | 3.5 |
| 26.5 | 3.4 |
| 26.8 | 3.3 |
| 27.2 | 3.3 |
| 28.0 | 3.2 |
| 29.0 | 3.1 |
| 29.4 | 3.0 |
| 30.5 | 2.9 |
| 31.1 | 2.9 |
| 31.8 | 2.8 |
| 32.9 | 2.7 |
| 33.6 | 2.7 |
| 34.1 | 2.6 |
| 37.3 | 2.4 |
| 37.9 | 2.4. |

A novel Compound 1 Mixture A can be identified by DSC, having two endotherms at 226.2° C. and 229.1° C. In some embodiments, Compound 1 Mixture A can be identified (i) by DSC having two endotherms at 226.2° C. and 229.1° C.; and (ii) by XRPD having one or more characteristic diffractions at angles (2 theta±0.2) of 9.6, 10.1, 15.4, 19.6, and 22.3. In some embodiments, Compound 1 Mixture A can be identified (i) by DSC having two endotherms at 226.2° C. and 229.1° C.; (ii) by XRPD having one or more characteristic diffractions at angles (2 theta±0.2) of 9.6, 10.1, 15.4, 19.6, and 22.3; and (iii) by XRPD not having a characteristic diffraction at an angle (2 theta±0.2) of 24.2.

A novel Compound 1 Form B can be identified by XRPD, having one or more characteristic diffractions at angles (2 theta±0.2) of 9.6, 10.1, 15.4, 19.6, and 22.3. In some embodiments, Compound 1 Form B can be identified by XRPD, having one or more characteristic diffractions at angles (2 theta±0.2) of 9.6, 10.1, 15.4, 19.6, and 22.3, corresponding to d-spacing (angstroms±0.2) of 9.2, 8.7, 5.7, 4.5, and 4.0. In some embodiments, Compound 1 Form B can be identified by XRPD, (i) having one or more characteristic diffractions at angles (2 theta±0.2) of 9.6, 10.1, 15.4, 19.6, and 22.3, and (ii) not having a characteristic diffraction at an angle (2 theta±0.2) of 24.2. In some embodiments, Compound 1 Form B can be identified by XRPD, (i) having one or more characteristic diffractions at angles (2 theta±0.2) of 15.4, 19.6, and 22.3, and (ii) not having a characteristic diffraction at an angle (2 theta±0.2) of 24.2. In some embodiments, Compound 1 Form B can be identified by XRPD, (i) having one or more characteristic diffractions at angles (2 theta±0.2) of 9.6, 10.1, 15.4, 19.6, and 22.3, and (ii) not having one or more characteristic diffractions at angles (2 theta±0.2) of 7.2, 8.5, 14.9, 16.1, and 17.8. In some embodiments, Compound 1 Form B can be identified by XRPD, (i) having one or more characteristic diffractions at angles (2 theta±0.2) of 9.6, 10.1, 15.4, 19.6, and 22.3; (ii) not having a characteristic diffraction at an angle (2 theta±0.2) of 24.2; and (iii) not having one or more characteristic diffractions at angles (2 theta±0.2) of 7.2, 8.5, 14.9, 16.1, and 17.8.

In some embodiments, Compound 1 Form B is characterized by an XRPD having one or more peaks at substantially the same angles (2 theta±0.2) of:

| |
|---|
| 9.6 |
| 10.1 |
| 10.7 |
| 12.6 |

| 2 Theta | |
|---|---|
| 13.9 | |
| 14.3 | |
| 15.4 | |
| 16.4 | |
| 16.6 | |
| 17.4 | |
| 18.2 | |
| 18.5 | |
| 19.6 | |
| 20.2 | |
| 22.1 | |
| 22.3 | |
| 23.4 | |
| 23.8 | |
| 25.0 | |
| 25.3 | |
| 26.5 | |
| 26.9 | |
| 28.0 | |
| 29.0 | |
| 29.5 | |
| 30.5 | |
| 31.1 | |
| 31.8 | |
| 32.9 | |
| 34.1 | |
| 37.3 | |
| 37.9. | |

In some embodiments, Compound 1 Form B is characterized by an XRPD having one or more peaks at substantially the same angles (2 theta±0.2), corresponding to d-spacing (angstroms±0.2) of:

| 2 Theta | d-spacing (Å) |
|---|---|
| 9.6 | 9.2 |
| 10.1 | 8.7 |
| 10.7 | 8.3 |
| 12.6 | 7.0 |
| 13.9 | 6.4 |
| 14.3 | 6.2 |
| 15.4 | 5.7 |
| 16.4 | 5.4 |
| 16.6 | 5.3 |
| 17.4 | 5.1 |
| 18.2 | 4.9 |
| 18.5 | 4.8 |
| 19.6 | 4.5 |
| 20.2 | 4.4 |
| 22.1 | 4.0 |
| 22.3 | 4.0 |
| 23.4 | 3.8 |
| 23.8 | 3.7 |
| 25.0 | 3.6 |
| 25.3 | 3.5 |
| 26.5 | 3.4 |
| 26.9 | 3.3 |
| 28.0 | 3.2 |
| 29.0 | 3.1 |
| 29.5 | 3.0 |
| 30.5 | 2.9 |
| 31.1 | 2.9 |
| 31.8 | 2.8 |
| 32.9 | 2.7 |
| 34.1 | 2.6 |
| 37.3 | 2.4 |
| 37.9 | 2.4. |

A novel Compound 1 Form B can be identified by DSC, having one endotherm at 225.7° C. In some embodiments, Compound 1 Form B can be identified (i) by DSC having one endotherm at 225.7° C.; and (ii) by XRPD having one or more characteristic diffractions at angles (2 theta±0.2) of 9.6, 10.1, 15.4, 19.6, and 22.3. In some embodiments, Compound 1 Form B can be identified (i) by DSC having one endotherm at 225.7° C.; (ii) by XRPD having one or more characteristic diffractions at angles (2 theta±0.2) of 9.6, 10.1, 15.4, 19.6, and 22.3; and (iii) by XRPD not having one or more characteristic diffractions at angles (2 theta±0.2) of 7.2, 8.5, 14.9, 16.1, and 17.8. In some embodiments, Compound 1 Form B can be identified (i) by DSC having one endotherm at 225.7° C.; (ii) by XRPD having one or more characteristic diffractions at angles (2 theta±0.2) of 9.6, 10.1, 15.4, 19.6, and 22.3; and (iii) by XRPD not having a characteristic diffraction at angle (2 theta±0.2) of 24.2. In some embodiments, Compound 1 Form B can be identified (i) by DSC having one endotherm at 225.7° C.; (ii) by XRPD having one or more characteristic diffractions at angles (2 theta±0.2) of 9.6, 10.1, 15.4, 19.6, and 22.3; and (iii) by XRPD not having one or more characteristic diffractions at angles (2 theta±0.2) of 7.2, 8.5, 14.9, 16.1, 17.8, and 24.2. In some embodiments, Compound 1 Form B is substantially free of Form C and Form X.

A novel Compound 1 Form C can be identified by XRPD, having one or more characteristic diffractions at angles (2 theta±0.2) of 9.6, 15.4, 19.6, 22.3, and 26.6. In some embodiments, Compound 1 Form C can be identified by XRPD, having one or more characteristic diffractions at angles (2 theta±0.2) of 9.6, 15.4, 19.6, 22.3, 24.2, and 26.6. In some embodiments, Compound 1 Form C can be identified by XRPD, having one or more characteristic diffractions at angles (2 theta±0.2) of 9.6, 15.4, 19.6, 22.3, and 26.6, corresponding to d-spacing (angstroms±0.2) of 9.3, 5.7, 4.5, 4.0, and 3.3.

In some embodiments, Compound 1 Form C is characterized by an XRPD having one or more peaks at substantially the same angles (2 theta±0.2) of:

| 2 Theta |
|---|
| 9.6 |
| 10.1 |
| 10.9 |
| 13.5 |
| 13.9 |
| 14.3 |
| 15.5 |
| 15.9 |
| 16.3 |
| 16.8 |
| 17.5 |
| 18.1 |
| 18.4 |
| 18.9 |
| 19.6 |
| 22.2 |
| 24.2 |
| 24.9 |
| 26.6 |
| 27.9 |
| 30.5 |
| 31.1 |
| 35.5 |
| 38.7 |

In some embodiments, Compound 1 Form C is characterized by an XRPD having one or more peaks at substantially the same angles (2 theta±0.2), corresponding to d-spacing (angstroms±0.2) of:

| 2 Theta | d-spacing (Å) |
|---|---|
| 9.6 | 9.3 |
| 10.1 | 8.8 |
| 10.9 | 8.1 |

-continued

| 2 Theta | d-spacing (Å) |
|---|---|
| 13.5 | 6.6 |
| 13.9 | 6.4 |
| 14.3 | 6.2 |
| 15.5 | 5.7 |
| 15.9 | 5.6 |
| 16.3 | 5.4 |
| 16.8 | 5.3 |
| 17.5 | 5.1 |
| 18.1 | 4.9 |
| 18.4 | 4.8 |
| 18.9 | 4.7 |
| 19.6 | 4.5 |
| 22.2 | 4.0 |
| 24.2 | 3.7 |
| 24.9 | 3.6 |
| 26.6 | 3.3 |
| 27.9 | 3.2 |
| 30.5 | 2.9 |
| 31.1 | 2.9 |
| 35.5 | 2.5 |
| 38.7 | 2.3 |

A novel Compound 1 Form C can be identified by DSC, having two endotherms at 101.1° C. and 224.0° C. In some embodiments, Compound 1 Form C can be identified (i) by DSC having two endotherms at 101.1° C. and 224.0° C.; and (ii) by XRPD having one or more characteristic diffractions at angles (2 theta±0.2) of 9.6, 15.4, 19.6, 22.3, and 26.6. In some embodiments, Compound 1 Form C is substantially free of Form B and Form X.

A novel Compound 1 Form X can be identified by XRPD, having one or more characteristic diffractions at angles (2 theta±0.2) of 7.2, 8.5, 14.9, 16.1, and 17.8. In some embodiments, Compound 1 Form X can be identified by XRPD, having one or more characteristic diffractions at angles (2 theta±0.2) of 7.2, 8.5, 14.9, 16.1, and 17.8, corresponding to d-spacing (angstroms±0.2) of 12.2, 10.4, 6.0, 5.5, and 5.0, respectively.

In some embodiments, Compound 1 Form X is characterized by an XRPD having one or more peaks at substantially the same angles (2 theta±0.2) of:

7.2
8.1
8.5
12.7
13.1
13.5
14.4
14.9
15.3
15.6
16.1
16.9
17.1
17.8
18.5
19.1
21.0
21.4
23.3
24.2
25.5
27.1
27.9
29.1
29.8
30.6
31.2
32.3
33.6
35.9
38.1.

In some embodiments, Compound 1 Form X is characterized by an XRPD having one or more peaks at substantially the same angles (2 theta±0.2), corresponding to d-spacing (angstroms±0.2) of:

| 2 Theta | d-spacing (Å) |
|---|---|
| 7.2 | 12.2 |
| 8.1 | 11.0 |
| 8.5 | 10.4 |
| 12.7 | 7.0 |
| 13.1 | 6.7 |
| 13.5 | 6.6 |
| 14.4 | 6.1 |
| 14.9 | 6.0 |
| 15.3 | 5.8 |
| 15.6 | 5.7 |
| 16.1 | 5.5 |
| 16.9 | 5.2 |
| 17.1 | 5.2 |
| 17.8 | 5.0 |
| 18.5 | 4.8 |
| 19.1 | 4.7 |
| 21.0 | 4.2 |
| 21.4 | 4.2 |
| 23.3 | 3.8 |
| 24.2 | 3.7 |
| 25.5 | 3.5 |
| 27.1 | 3.3 |
| 27.9 | 3.2 |
| 29.1 | 3.1 |
| 29.8 | 3.0 |
| 30.6 | 2.9 |
| 31.2 | 2.9 |
| 32.3 | 2.8 |
| 33.6 | 2.7 |
| 35.9 | 2.5 |
| 38.1 | 2.4. |

A novel Compound 1 Form X can be identified by DSC, having one endotherm at 232.9° C. In some embodiments, Compound 1 Form X can be identified (i) by DSC having one endotherm at 232.9° C.; and (ii) by XRPD having one or more characteristic diffractions at angles (2 theta±0.2) of 7.2, 8.5, 14.9, 16.1, and 17.8. In some embodiments, Compound 1 Form X is substantially free of Form B and Form C.

In some embodiments, the present disclosure provides a composition comprising amorphous and crystalline solid forms of Compound 1. In some embodiments, the composition comprises crystalline Compound 1 and amorphous Compound 1, wherein the amorphous Compound 1 is present in an amount selected from the following ranges: 90-99%, 80-89%, 70-79%, 60-69%, 50-59%, 40-49%, 30-39%, 20-29%, 10-19%, 1-9% and 0-0.99%.

In some embodiments, a crystalline form of Compound 1 is anhydrous. In some embodiments, an anhydrous crystalline form of Compound 1 is selected from Mixture A, Form B, and Form X. In some embodiments, an anhydrous crystalline form of Compound 1 is Mixture A. In some embodiments, an anhydrous crystalline form of Compound 1 is Form B. In some embodiments, an anhydrous crystalline form of Compound 1 is Form X. In some embodiments, an anhydrous crystalline form of Compound 1 is a mixture of Form B and another solid form (e.g., Mixture A).

In some embodiments, a crystalline form of Compound 1 is a hydrate. In some embodiments, a hydrate crystalline form of Compound 1 is Form C.

A pharmaceutical composition can comprise and/or be obtained from the solid form of Compound 1, designated as Form B, that produces an XRPD pattern having one or more diffractions at angles (2 theta±0.2) of 9.6, 10.1, 15.4, 19.6, and 22.3. In some embodiments, the pharmaceutical composition can comprise and/or be obtained from Compound 1 Form B, which can be identified by an XRPD pattern having one or more diffractions at angles (2 theta±0.2) of 9.6, 10.1, 15.4, 19.6, and 22.3, corresponding to d-spacing (angstroms±0.2) of 9.2, 8.7, 5.7, 4.5, and 4.0. In some embodiments, the pharmaceutical composition can comprise and/or be obtained from Compound 1 Form B, which can be identified by XRPD, (i) having one or more characteristic diffractions at angles (2 theta±0.2) of 9.6, 10.1, 15.4, 19.6, and 22.3; and (ii) not having a characteristic diffraction at an angle (2 theta±0.2) of 24.2. In some embodiments, the pharmaceutical composition can comprise and/or be obtained from Compound 1 Form B, which can be identified by XRPD, (i) having one or more characteristic diffractions at angles (2 theta±0.2) of 15.4, 19.6, and 22.3; and (ii) not having a characteristic diffraction at an angle (2 theta±0.2) of 24.2. In some embodiments, the pharmaceutical composition can comprise and/or be obtained from Compound 1 Form B, which can be identified by XRPD (i) having one or more characteristic diffractions at angles (2 theta±0.2) of 9.6, 10.1, 15.4, 19.6, and 22.3, and (ii) not having one or more characteristic diffractions at angles (2 theta±0.2) of 7.2, 8.5, 14.9, 16.1, and 17.8. In some embodiments, the pharmaceutical composition can comprise and/or be obtained from Compound 1 Form B, which can be identified by XRPD, (i) having one or more characteristic diffractions at angles (2 theta±0.2) of 9.6, 10.1, 15.4, 19.6, and 22.3; (ii) not having a characteristic diffraction at an angle (2 theta±0.2) of 24.2; and (iii) not having one or more characteristic diffractions at angles (2 theta±0.2) of 7.2, 8.5, 14.9, 16.1, and 17.8. In some embodiments, the pharmaceutical composition can comprise any one of the solid forms of Compound 1 described herein. In some embodiments, the pharmaceutical composition is substantially free of Compound 1 Form X. In some embodiments, the pharmaceutical composition can comprise and/or be obtained from a solid form consisting of Compound 1 Form B.

A pharmaceutical composition can comprise and/or be obtained from the solid form of Compound 1, designated as Form B, that can be identified by DSC, having one endotherm at 225.7° C. In some embodiments, the pharmaceutical composition can comprise and/or be obtained from Compound 1 Form B, which can be identified (i) by DSC having one endotherm at 225.7° C.; and (ii) by XRPD having one or more characteristic diffractions at angles (2 theta±0.2) of 9.6, 10.1, 15.4, 19.6, and 22.3. In some embodiments, the pharmaceutical composition can comprise and/or be obtained from Compound 1 Form B, which can be identified (i) by DSC having one endotherm at 225.7° C.; (ii) by XRPD having one or more characteristic diffractions at angles (2 theta±0.2) of 9.6, 10.1, 15.4, 19.6, and 22.3; and (iii) by XRPD not having one or more characteristic diffractions at angles (2 theta±0.2) of 7.2, 8.5, 14.9, 16.1, 17.8, and 24.2.

Pharmaceutical compositions reported herein can be combined with a pharmaceutically acceptable carrier or excipient. In some embodiments, pharmaceutical compositions reported herein can be provided in a unit dosage form container (e.g., in a vial or bag or the like). In some embodiments, pharmaceutical compositions reported herein can be provided in an oral dosage form. In some embodiments, an oral dosage form is a capsule. In some embodiments, an oral dosage form is a tablet.

In some embodiments, the present disclosure provides methods of inhibiting FASN, comprising administering a solid form of Compound 1 to a subject. In some embodiments, the present disclosure provides methods of treating a disease, disorder, or condition responsive to inhibition of FASN, comprising administering a solid form of Compound 1 to a subject in need thereof. In some embodiments, the disease, disorder, or condition is non-alcoholic steatohepatitis (NASH).

In some embodiments, the present disclosure relates to:

1. Crystalline (4-(2-fluoro-4-(1-methyl-1H-benzo[d]imidazol-5-yl)benzoyl)piperazin-1-yl)(1-hydroxycyclopropyl)methanone.

2. A solid form of Compound 1:

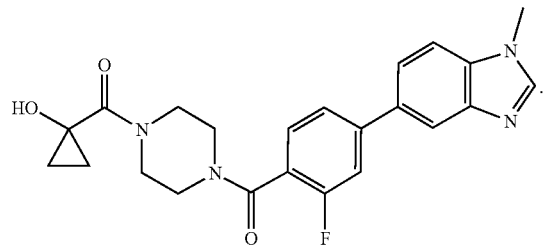 [SMILES: Cn1cnc2cc(-c3ccc(C(=O)N4CCN(C(=O)C5(O)CC5)CC4)c(F)c3)ccc21]

3. The solid form of embodiment 2, wherein the solid form is characterized by an XRPD pattern having diffractions at angles (2 theta±0.2) of 9.6, 10.1, 15.4, 19.6, and 22.3.

4. The solid form of embodiment 3, wherein the solid form is characterized by an XRPD pattern having diffractions at angles (2 theta±0.2) of 9.6, 10.1, 15.4, 19.6, and 22.3, and not having one or more diffractions at angles (2 theta±0.2) of 7.2, 8.5, 14.9, 16.1, and 17.8.

5. The solid form of embodiment 3 or 4, wherein the solid form is characterized by an XRPD pattern having diffractions at angles (2 theta±0.2) of 9.6, 10.1, 15.4, 19.6, and 22.3 and not having a diffraction at angle (2 theta±0.2) of 24.2.

6. The solid form of any one of the preceding embodiments, wherein the solid form is characterized by an XRPD pattern having diffractions at angles (2 theta±0.2) of 9.6, 10.1, 15.4, 19.6, and 22.3, corresponding to d-spacing (Å±0.2) of 9.2, 8.7, 5.7, 4.5, and 4.0, respectively.

7. The solid form of any one of the preceding embodiments, wherein the solid form is characterized by an XRPD pattern having diffractions at angles (2 theta±0.2) of:

| |
|---|
| 9.6 |
| 10.1 |
| 10.7 |
| 12.6 |
| 13.9 |
| 14.3 |
| 15.4 |
| 16.4 |
| 16.6 |
| 17.4 |
| 18.2 |
| 18.5 |
| 19.6 |
| 20.2 |
| 22.1 |

-continued

| |
|---|
| 22.3 |
| 23.4 |
| 23.8 |
| 25.0 |
| 25.3 |
| 26.5 |
| 26.9 |
| 28.0 |
| 29.0 |
| 29.5 |
| 30.5 |
| 31.1 |
| 31.8 |
| 32.9 |
| 34.1 |
| 37.3 |
| 37.9. |

8. The solid form of any one of the preceding embodiments, wherein the solid form is characterized by an XRPD pattern having diffractions at angles (2 theta±0.2) corresponding to d-spacing (Å±0.2) of:

| 2 Theta | d-spacing (Å) |
|---|---|
| 9.6 | 9.2 |
| 10.1 | 8.7 |
| 10.7 | 8.3 |
| 12.6 | 7.0 |
| 13.9 | 6.4 |
| 14.3 | 6.2 |
| 15.4 | 5.7 |
| 16.4 | 5.4 |
| 16.6 | 5.3 |
| 17.4 | 5.1 |
| 18.2 | 4.9 |
| 18.5 | 4.8 |
| 19.6 | 4.5 |
| 20.2 | 4.4 |
| 22.1 | 4.0 |
| 22.3 | 4.0 |
| 23.4 | 3.8 |
| 23.8 | 3.7 |
| 25.0 | 3.6 |
| 25.3 | 3.5 |
| 26.5 | 3.4 |
| 26.9 | 3.3 |
| 28.0 | 3.2 |
| 29.0 | 3.1 |
| 29.5 | 3.0 |
| 30.5 | 2.9 |
| 31.1 | 2.9 |
| 31.8 | 2.8 |
| 32.9 | 2.7 |
| 34.1 | 2.6 |
| 37.3 | 2.4 |
| 37.9 | 2.4. |

9. The solid form of any one of the preceding embodiments, wherein the solid form is characterized by an XRPD pattern expressed in terms of angles (2 theta±0.2) and obtained with a diffractometer according to one or more parameters from Table 1, and wherein the X-ray powder diffraction pattern comprises diffractions at angles (2 theta±0.2) of 9.6, 10.1, 15.4, 19.6, and 22.3.

10. The solid form of any one of the preceding embodiments, wherein the solid form is characterized by a DSC endotherm having an endotherm at about 226° C.

11. The solid form of any one of the preceding embodiments, wherein the solid form is characterized by a DSC endotherm expressed in terms of degrees and obtained with a calorimeter according to one or more parameters from Table 3, wherein the DSC endotherm is at about 226° C.

12. The solid form of any one of the preceding embodiments, wherein the solid form is characterized by a TGA with a weight loss of about 0.5% between 21° C. and 100° C.

13. The solid form of any one of the preceding embodiments, wherein the solid form is characterized by a DVS of about 0.5% water by weight below 95% relative humidity.

14. The solid form of any one of the preceding embodiments, wherein the solid form is Solid Form B.

15. The solid form of embodiment 2, wherein the solid form is characterized by an XRPD pattern having diffractions at angles (2 theta±0.2) of 9.6, 15.4, 19.6, 22.3, and 26.6.

16. The solid form of embodiment 15, wherein the solid form is characterized by an XRPD pattern having diffractions at angles (2 theta±0.2) of 9.6, 15.4, 19.6, 22.3, and 26.6, corresponding to d-spacing (Å±0.2) of 9.3, 5.7, 4.5, 4.0, and 3.3, respectively.

17. The solid form of embodiment 15 or 16, wherein the solid form is characterized by an XRPD pattern having diffractions at angles (2 theta±0.2) of:

| |
|---|
| 9.6 |
| 10.1 |
| 10.9 |
| 13.5 |
| 13.9 |
| 14.3 |
| 15.5 |
| 15.9 |
| 16.3 |
| 16.8 |
| 17.5 |
| 18.1 |
| 18.4 |
| 18.9 |
| 19.6 |
| 22.2 |
| 24.2 |
| 24.9 |
| 26.6 |
| 27.9 |
| 30.5 |
| 31.1 |
| 35.5 |
| 38.7 |

18. The solid form of any one of embodiments 15-17, wherein the solid form is characterized by an XRPD pattern having diffractions at angles (2 theta±0.2) corresponding to d-spacing (Å±0.2) of:

| 2 Theta | d-spacing (Å) |
|---|---|
| 9.6 | 9.3 |
| 10.1 | 8.8 |
| 10.9 | 8.1 |
| 13.5 | 6.6 |
| 13.9 | 6.4 |
| 14.3 | 6.2 |
| 15.5 | 5.7 |
| 15.9 | 5.6 |
| 16.3 | 5.4 |
| 16.8 | 5.3 |
| 17.5 | 5.1 |
| 18.1 | 4.9 |
| 18.4 | 4.8 |
| 18.9 | 4.7 |
| 19.6 | 4.5 |
| 22.2 | 4.0 |
| 24.2 | 3.7 |
| 24.9 | 3.6 |

-continued

| 2 Theta | d-spacing (Å) |
|---|---|
| 26.6 | 3.3 |
| 27.9 | 3.2 |
| 30.5 | 2.9 |
| 31.1 | 2.9 |
| 35.5 | 2.5 |
| 38.7 | 2.3 |

19. The solid form of any one of embodiments 15-18, wherein the solid form is characterized by an X-ray powder diffraction pattern expressed in terms of angles (2 theta±0.2) and obtained with a diffractometer according to one or more parameters from Table 1, and wherein the X-ray powder diffraction pattern comprises diffractions at angles (2 theta±0.2) of 9.6, 15.4, 19.6, 22.3, and 26.6.

20. The solid form of any one of embodiments 15-19, wherein the solid form is characterized by a DSC endotherm having two endotherms at about 101.1° C. and about 224.0° C.

21. The solid form of any one of embodiments 15-20, wherein the solid form is characterized by a DSC endotherm expressed in terms of degrees and obtained with a calorimeter according to one or more parameters from Table 3, wherein the DSC endotherm is at about 101.1° C. and about 224.0° C.

22. The solid form of any one embodiments 15-21, wherein the solid form is characterized by a TGA with a weight loss of about 5.77% between 21° C. and 100° C.

23. The solid form of any one of embodiments 15-22, wherein the solid form is Solid Form C.

24. The solid form of embodiment 2, wherein the solid form is characterized by an XRPD pattern having diffractions at angles (2 theta±0.2) of 7.2, 8.5, 14.9, 16.1, and 17.8.

25. The solid form of embodiment 24, wherein the solid form is characterized by an XRPD pattern having diffractions at angles (2 theta±0.2) of 7.2, 8.5, 14.9, 16.1, and 17.8, corresponding to d-spacing (Å±0.2) of 12.2, 10.4, 6.0, 5.5, and 5.0, respectively.

26. The solid form of embodiment 24 or 25, wherein the solid form is characterized by an XRPD pattern having diffractions at angles (2 theta±0.2) of:

| |
|---|
| 7.2 |
| 8.1 |
| 8.5 |
| 12.7 |
| 13.1 |
| 13.5 |
| 14.4 |
| 14.9 |
| 15.3 |
| 15.6 |
| 16.1 |
| 16.9 |
| 17.1 |
| 17.8 |
| 18.5 |
| 19.1 |
| 21.0 |
| 21.4 |
| 23.3 |
| 24.2 |
| 25.5 |
| 27.1 |
| 27.9 |
| 29.1 |
| 29.8 |
| 30.6 |
| 31.2 |
| 32.3 |
| 33.6 |
| 35.9 |
| 38.1. |

27. The solid form of any one of embodiments 24-26, wherein the solid form is characterized by an XRPD pattern having diffractions at angles (2 theta±0.2) corresponding to d-spacing (Å±0.2) of:

| 2 Theta | d-spacing (Å) |
|---|---|
| 7.2 | 12.2 |
| 8.1 | 11.0 |
| 8.5 | 10.4 |
| 12.7 | 7.0 |
| 13.1 | 6.7 |
| 13.5 | 6.6 |
| 14.4 | 6.1 |
| 14.9 | 6.0 |
| 15.3 | 5.8 |
| 15.6 | 5.7 |
| 16.1 | 5.5 |
| 16.9 | 5.2 |
| 17.1 | 5.2 |
| 17.8 | 5.0 |
| 18.5 | 4.8 |
| 19.1 | 4.7 |
| 21.0 | 4.2 |
| 21.4 | 4.2 |
| 23.3 | 3.8 |
| 24.2 | 3.7 |
| 25.5 | 3.5 |
| 27.1 | 3.3 |
| 27.9 | 3.2 |
| 29.1 | 3.1 |
| 29.8 | 3.0 |
| 30.6 | 2.9 |
| 31.2 | 2.9 |
| 32.3 | 2.8 |
| 33.6 | 2.7 |
| 35.9 | 2.5 |
| 38.1 | 2.4. |

28. The solid form of any one of embodiments 24-27, wherein the solid form is characterized by an XRPD pattern expressed in terms of angles (2 theta±0.2) and obtained with a diffractometer according to one or more parameters from Table 1, and wherein the X-ray powder diffraction pattern comprises diffractions at angles (2 theta±0.2) of 7.2, 8.5, 14.9, 16.1, and 17.8.

29. The solid form of any one of embodiments 24-28, wherein the solid form is characterized by a DSC endotherm having an endotherm at about 232.9° C.

30. The solid form of any one embodiments 24-29, wherein the solid form is characterized by a DSC endotherm expressed in terms of degrees and obtained with a calorimeter according to one or more parameters from Table 3, wherein the DSC endotherm is at about 232.9° C.

31. The solid form of any one embodiments 24-30, wherein the solid form is characterized by a TGA with a weight loss of about 0.47% between 21° C. and 150° C.

32. The solid form of any one of embodiments 24-31, wherein the solid form is Solid Form X.

33. A composition comprising a mixture of solid forms of Compound 1:

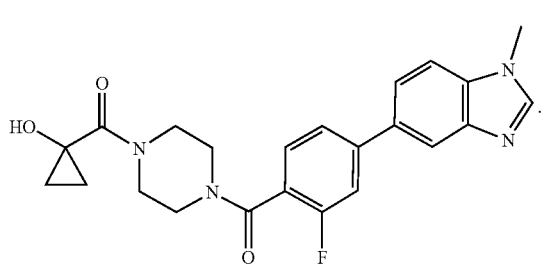

34. The composition of embodiment 33, wherein the composition is characterized by an XRPD pattern having diffractions at angles (2 theta±0.2) of 9.6, 10.1, 15.4, 19.6, and 22.3.

35. The composition of embodiment 33 or 34, wherein the solid form mixture is characterized by an XRPD pattern having diffractions at angles (2 theta±0.2) of 9.6, 10.1, 15.4, 19.6, and 22.3, corresponding to d-spacing (Å±0.2) of 9.3, 8.7, 5.7, 4.5, and 4.0, respectively.

36. The composition of any one of embodiments 33-35, wherein the solid form mixture is characterized by an XRPD pattern having diffractions at angles (2 theta±0.2) corresponding to d-spacing (Å±0.2) of:

| |
|---|
| 7.9 |
| 9.6 |
| 10.1 |
| 10.7 |
| 12.6 |
| 13.4 |
| 13.9 |
| 14.3 |
| 15.4 |
| 16.3 |
| 16.8 |
| 17.4 |
| 18.5 |
| 19.6 |
| 20.2 |
| 21.0 |
| 21.4 |
| 22.1 |
| 22.2 |
| 23.4 |
| 23.8 |
| 25.0 |
| 25.3 |
| 26.5 |
| 26.8 |
| 27.2 |
| 28.0 |
| 29.0 |
| 29.4 |
| 30.5 |
| 31.1 |
| 31.8 |
| 32.9 |
| 33.6 |
| 34.1 |
| 37.3 |
| 37.9 |

37. The composition of any one of embodiments 33-36, wherein the solid form is characterized by an XRPD pattern having diffractions at angles (2 theta±0.2) corresponding to d-spacing (Å±0.2) of:

| 2 Theta | d-spacing (Å) |
|---|---|
| 7.9 | 11.1 |
| 9.6 | 9.3 |
| 10.1 | 8.7 |
| 10.7 | 8.3 |
| 12.6 | 7.0 |
| 13.4 | 6.6 |
| 13.9 | 6.4 |
| 14.3 | 6.2 |
| 15.4 | 5.7 |
| 16.3 | 5.4 |
| 16.8 | 5.3 |
| 17.4 | 5.1 |
| 18.5 | 4.8 |
| 19.6 | 4.5 |
| 20.2 | 4.4 |
| 21.0 | 4.2 |
| 21.4 | 4.2 |
| 22.1 | 4.0 |
| 22.2 | 4.0 |
| 23.4 | 3.8 |
| 23.8 | 3.7 |
| 25.0 | 3.6 |
| 25.3 | 3.5 |
| 26.5 | 3.4 |
| 26.8 | 3.3 |
| 27.2 | 3.3 |
| 28.0 | 3.2 |
| 29.0 | 3.1 |
| 29.4 | 3.0 |
| 30.5 | 2.9 |
| 31.1 | 2.9 |
| 31.8 | 2.8 |
| 32.9 | 2.7 |
| 33.6 | 2.7 |
| 34.1 | 2.6 |
| 37.3 | 2.4 |
| 37.9 | 2.4. |

38. The solid form of any one of embodiments 33-37, wherein the solid form is characterized by an XRPD pattern expressed in terms of angles (2 theta±0.2) and obtained with a diffractometer according to one or more parameters from Table 1, and wherein the X-ray powder diffraction pattern comprises diffractions at angles (2 theta±0.2) of 9.6, 10.1, 15.4, 19.6, and 22.3.

39. The composition of any one of embodiments 33-38, wherein the solid form mixture is characterized by a DSC endotherm having two endotherms at about 226.2° C. and about 229.1° C.

40. The solid form of any one embodiments 33-39, wherein the solid form is characterized by a DSC endotherm expressed in terms of degrees and obtained with a calorimeter according to one or more parameters from Table 3, wherein the DSC endotherm is at about 226.2° C. and about 229.1° C.

41. The composition of any one embodiments 33-40, wherein the solid form mixture is characterized by a TGA with a weight loss of about 1.73% between 21° C. and 150° C.

42. The composition of any one of embodiments 33-41, wherein the solid form mixture is Solid Form Mixture A.

43. A pharmaceutical composition comprising a solid form of Compound 1:

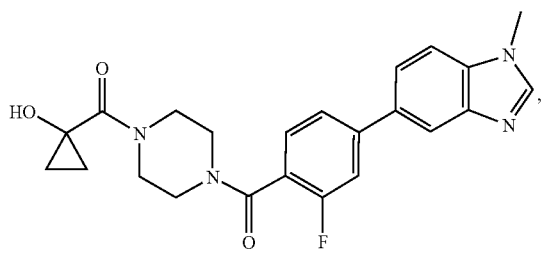 [SMILES: Cn1cnc2cc(-c3ccc(C(=O)N4CCN(C(=O)C5(O)CC5)CC4)c(F)c3)ccc21]

and a pharmaceutically acceptable carrier.

44. The pharmaceutical composition of embodiment 43, wherein the solid form is characterized by an XRPD pattern having diffractions at angles (2 theta±0.2) of 9.6, 10.1, 15.4, 19.6, and 22.3.

45. The pharmaceutical composition of embodiment 43 or 44, wherein the solid form is characterized by an XRPD pattern having diffractions at angles (2 theta±0.2) of 9.6, 10.1, 15.4, 19.6, and 22.3, and not having one or more diffractions at angles (2 theta±0.2) of 7.2, 8.5, 14.9, 16.1, and 17.8.

46. The pharmaceutical composition of any one of embodiments 43-45, wherein the solid form is characterized by an XRPD pattern having diffractions at angles (2 theta±0.2) of 9.6, 10.1, 15.4, 19.6, and 22.3 and not having a diffraction at angle (2 theta±0.2) of 24.2.

47. The pharmaceutical composition of any one of embodiments 43-46, wherein the solid form is characterized by an XRPD pattern having diffractions at angles (2 theta±0.2) of 9.6, 10.1, 15.4, 19.6, and 22.3, corresponding to d-spacing (Å±0.2) of 9.2, 8.7, 5.7, 4.5, and 4.0, respectively.

48. The pharmaceutical composition of any one of embodiments 43-47, wherein the solid form is characterized by an XRPD pattern having diffractions at angles (2 theta±0.2) of:

| |
|---|
| 9.6 |
| 10.1 |
| 10.7 |
| 12.6 |
| 13.9 |
| 14.3 |
| 15.4 |
| 16.4 |
| 16.6 |
| 17.4 |
| 18.2 |
| 18.5 |
| 19.6 |
| 20.2 |
| 22.1 |
| 22.3 |
| 23.4 |
| 23.8 |
| 25.0 |
| 25.3 |
| 26.5 |
| 26.9 |
| 28.0 |
| 29.0 |
| 29.5 |
| 30.5 |
| 31.1 |
| 31.8 |
| 32.9 |
| 34.1 |
| 37.3 |
| 37.9. |

49. The pharmaceutical composition of any one of embodiments 43-48, wherein the solid form is characterized by an XRPD pattern having diffractions at angles (2 theta±0.2) corresponding to d-spacing (Å±0.2) of:

| 2 Theta | d-spacing (Å) |
|---|---|
| 9.6 | 9.2 |
| 10.1 | 8.7 |
| 10.7 | 8.3 |
| 12.6 | 7.0 |
| 13.9 | 6.4 |
| 14.3 | 6.2 |
| 15.4 | 5.7 |
| 16.4 | 5.4 |
| 16.6 | 5.3 |
| 17.4 | 5.1 |
| 18.2 | 4.9 |
| 18.5 | 4.8 |
| 19.6 | 4.5 |
| 20.2 | 4.4 |
| 22.1 | 4.0 |
| 22.3 | 4.0 |
| 23.4 | 3.8 |
| 23.8 | 3.7 |
| 25.0 | 3.6 |
| 25.3 | 3.5 |
| 26.5 | 3.4 |
| 26.9 | 3.3 |
| 28.0 | 3.2 |
| 29.0 | 3.1 |
| 29.5 | 3.0 |
| 30.5 | 2.9 |
| 31.1 | 2.9 |
| 31.8 | 2.8 |
| 32.9 | 2.7 |
| 34.1 | 2.6 |
| 37.3 | 2.4 |
| 37.9 | 2.4. |

50. The solid form of any one of embodiments 43-49, wherein the solid form is characterized by an XRPD pattern expressed in terms of angles (2 theta±0.2) and obtained with a diffractometer according to one or more parameters from Table 1, and wherein the X-ray powder diffraction pattern comprises diffractions at angles (2 theta±0.2) of 9.6, 10.1, 15.4, 19.6, and 22.3.

51. The pharmaceutical composition of any one of embodiments 43-50, wherein the solid form is characterized by a DSC endotherm having an endotherm at about 226° C.

52. The solid form of any one of embodiments 43-51, wherein the solid form is characterized by a DSC endotherm expressed in terms of degrees and obtained with a calorimeter according to one or more parameters from Table 3, wherein the DSC endotherm is at about 226° C.

53. The pharmaceutical composition of any one of embodiments 43-52, wherein the solid form is characterized by a TGA with a weight loss of about 0.5% between 21° C. and 100° C.

54. The pharmaceutical composition of any one of embodiments 43-53, wherein the solid form is characterized by a DVS of about 0.5% water by weight below 95% relative humidity.

55. The pharmaceutical composition of any one of embodiments 43-54, wherein the solid form is Solid Form B.

56. A process for preparing Solid Form B of (4-(2-fluoro-4-(1-methyl-1H-benzo[d]imidazol-5-yl) benzoyl)piperazin- 1-yl)(1-hydroxycyclopropyl)methanone (Compound 1) comprising suspending at least one of Mixture A, Form C, and Form X in a solvent to provide a slurry, and maintaining the slurry for a period of time under conditions effective to generate Solid Form B of Compound 1.

57. The process of embodiment 56, wherein the solvent is selected from the group consisting of ethyl acetate (EtOAc), acetonitrile (ACN), heptane, isopropyl alcohol (IPA), and ethanol (EtOH).

58. The process of embodiment 56 or 57, wherein the slurry is heated to a temperature from about 50° C. to about 100° C. after suspension in the solvent.

59. The process of any one of embodiments 56-58, further comprising isolating Solid Form B of Compound 1 from the slurry.

60. A solid form obtained by a process described herein.

61. The solid form of embodiment 60, wherein the solid form is Form B.

62. The solid form of embodiment 60, wherein the solid form is Form C.

63. The solid form of embodiment 60, wherein the solid form is Form X.

64. A composition obtained by a process described herein.

65. The composition of embodiment 64, wherein the composition is Solid Form Mixture A.

In some embodiments, the present disclosure relates to:

1. Crystalline (4-(2-fluoro-4-(1-methyl-1H-benzo[d]imidazol-5-yl)benzoyl)piperazin-1-yl)(1- hydroxycyclopropyl)methanone.

2. A solid form of Compound 1:

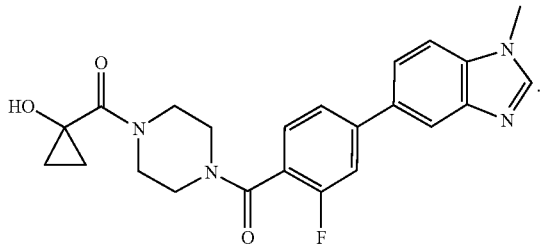 [SMILES: Cn1cnc2cc(-c3ccc(C(=O)N4CCN(C(=O)C5(O)CC5)CC4)c(F)c3)ccc21]

3. The solid form of embodiment 2, wherein the solid form is characterized by an XRPD pattern having diffractions at angles (2 theta±0.2) of 9.6, 10.1, 15.4, 19.6, and 22.3.

4. The solid form of embodiment 3, wherein the solid form is characterized by an XRPD pattern having diffractions at angles (2 theta±0.2) of 9.6, 10.1, 15.4, 19.6, and 22.3 and not having a diffraction at angle (2 theta±0.2) of 24.2.

5. The solid form of embodiment 2, wherein the solid form is characterized by an XRPD pattern having diffractions at angles (2 theta±0.2) of 15.4, 19.6, and 22.3 and not having a diffraction at angle (2 theta±0.2) of 24.2.

6. The solid form of any one of the preceding embodiments, wherein the solid form is characterized by a DSC endotherm having an endotherm at about 226° C.

7. The solid form of any one of the preceding embodiments, wherein the solid form is characterized by a TGA with a weight loss of about 0.5% between 21° C. and 100° C.

8. The solid form of any one of the preceding embodiments, wherein the solid form is characterized by a DVS of about 0.5% water by weight below 95% relative humidity.

9. The solid form of any one of the preceding embodiments, wherein the solid form is Solid Form B.

10. The solid form of embodiment 2, wherein the solid form is characterized by an XRPD pattern having diffractions at angles (2 theta±0.2) of 9.6, 15.4, 19.6, 22.3, and 26.6.

11. The solid form of embodiment 2, wherein the solid form is characterized by an XRPD pattern having diffractions at angles (2 theta±0.2) of 9.6, 15.4, 19.6, 22.3, 24.2, and 26.6.

12. The solid form of embodiment 2, wherein the solid form is characterized by an XRPD pattern having diffractions at angles (2 theta±0.2) of 7.2, 8.5, 14.9, 16.1, and 17.8.

13. A composition comprising a mixture of solid forms of Compound 1:

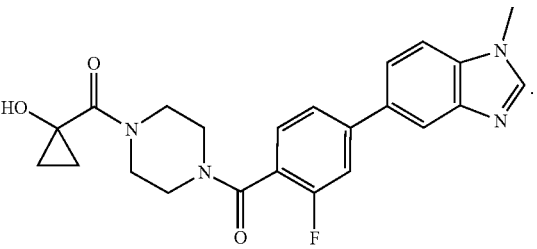 [SMILES: Cn1cnc2cc(-c3ccc(C(=O)N4CCN(C(=O)C5(O)CC5)CC4)c(F)c3)ccc21]

14. The composition of embodiment 13, wherein the composition is characterized by an XRPD pattern having diffractions at angles (2 theta±0.2) of 9.6, 10.1, 15.4, 19.6, and 22.3.

15. The composition of embodiment 13, wherein the composition is characterized by an XRPD pattern having diffractions at angles (2 theta±0.2) of 9.6, 10.1, 15.4, 19.6, 21.0, and 22.3.

16. A pharmaceutical composition comprising a solid form of Compound 1:

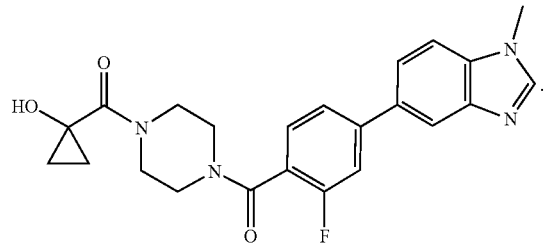

and a pharmaceutically acceptable carrier.

17. The pharmaceutical composition of embodiment 16, wherein the solid form of Compound 1 is the solid form of any one of embodiments 1-12.

18. The pharmaceutical composition of embodiment 16, wherein the solid form is characterized by an XRPD pattern having diffractions at angles (2 theta±0.2) of 9.6, 10.1, 15.4, 19.6, and 22.3.

19. The pharmaceutical composition of any one of embodiments 16-18, wherein the solid form is characterized by an XRPD pattern having diffractions at angles (2 theta±0.2) of 9.6, 10.1, 15.4, 19.6, and 22.3 and not having a diffraction at angle (2 theta±0.2) of 24.2.

20. The pharmaceutical composition of embodiment 16, wherein the solid form is characterized by an XRPD pattern having diffractions at angles (2 theta±0.2) of 15.4, 19.6, and 22.3 and not having a diffraction at angle (2 theta±0.2) of 24.2.

21. The pharmaceutical composition of any one of embodiments 16-20, wherein the solid form is Solid Form B.

22. The pharmaceutical composition of any one of embodiments 16-21, wherein the pharmaceutical composition is substantially free of Solid Form X.

23. The pharmaceutical composition of embodiment 16, wherein the solid form consists of Solid Form B.

24. A process for preparing Solid Form B of (4-(2-fluoro-4-(1-methyl-1H-benzo[d]imidazol-5-yl)benzoyl)piperazin-1-yl) (1-hydroxycyclopropyl)methanone (Compound 1) comprising suspending at least one of Mixture A, Form C, and Form X in a solvent to provide a slurry, and maintaining the slurry for a period of time under conditions effective to generate Solid Form B of Compound 1.

25. The process of embodiment 24, wherein the solvent is selected from the group consisting of ethyl acetate (EtOAc), acetonitrile (ACN), heptane, isopropyl alcohol (IPA), and ethanol (EtOH).

26. The process of embodiment 24 or 25, wherein the slurry is heated to a temperature from about 50° C. to about 100° C. after suspension in the solvent.

27. The process of any one of embodiments 24-26, further comprising isolating Solid Form B of Compound 1 from the slurry.

28. A solid form of Compound 1:

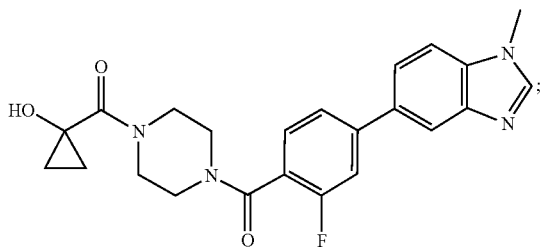 [SMILES: Cn1cnc2cc(-c3ccc(C(=O)N4CCN(C(=O)C5(O)CC5)CC4)c(F)c3)ccc21]

wherein the solid form is the form that would be obtained by a process comprising:
  suspending at least one of Mixture A, Form C, and Form X of Compound 1 in a solvent selected from a group consisting of ethyl acetate (EtOAc), acetonitrile (ACN), heptane, isopropyl alcohol (IPA), and ethanol (EtOH) to provide a slurry; and
  maintaining the slurry for a period of at least 5 hours to afford the solid form of Compound 1.

29. The solid form of embodiment 28, wherein the slurry is heated to a temperature from about 50° C. to about 100° C. after suspension in the solvent.

30. The solid form of embodiment 28 or 29, further comprising isolating the solid form of Compound 1 from the slurry.

EXAMPLES

Instrumentation and Methods

Unless otherwise indicated, the following instrumentation and methods were used in the working examples described herein.

X-ray Powder Diffraction (XRPD)

High resolution XRPD experiments were performed with Panalytical X'Pert[3] Powder XRPD on a Si zero-background holder. The 2θposition was calibrated against Panalytical 640 Si powder standard. Details of the XRPD method are listed in Table 1 below:

TABLE 1

| Parameters for Reflection Mode | |
| --- | --- |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 30°-40° |
| Step size (°2TH) | 0.0262606 |
| Scan speed (°/s) | 0.066482 |

Peaks are reported as diffraction angles at 2 theta, with d-spacing measured in angstroms.

Thermal Analysis

TGA experiments were performed on TA Q500 TGA from TA Instruments. Samples were heated at 10° C./min from about 20° C. to about 350° C. using dry nitrogen to purge the system. The details of the method are provided in Table 2, below:

TABLE 2

| Parameters | TGA |
| --- | --- |
| Temperature | RT-350° C. |
| Ramp rate | 10° C./min |
| Purge gas | $N_2$ |

DSC experiments were performed on TA Q2000 DSC from TA Instruments. Samples were heated at 10° C. to about 350° C. using dry nitrogen to purge the system. The details of the method are providing in Table 3, below:

TABLE 3

| Parameters | DSC |
| --- | --- |
| Temperature | RT-350° C. |
| Ramp rate | 10° C./min |
| Purge gas | $N_2$ |

Dynamic Vapor Sorption

DVS was obtained using a Surface Measurement System (SMS) DVS Intrinsic. The details of the method are providing in Table 4, below:

TABLE 4

| Parameters | Values |
| --- | --- |
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 360 min |
| Relative humidity (RH) range | 20% RH-95% RH-0% RH-95% RH |
| Relative humidity (RH) step size | 10% |

High Pressure Liquid Chromatography

High Pressure Liquid Chromatography (HPLC) data was obtained according to Table 5, below:

TABLE 5

| HPLC Method | Parameters | |
|---|---|---|
| Instrument | Agilent 1100 HPLC with DAD detector | |
| Column | Waters Xbridge C18, 100Å, 3.5 μm, 4.6 × mm | |
| Mobile Phase | A: 0.1% TFA in H$_2$O B: 0.1% TFA in acetonitrile | |
| | Time (min) | B % |
| Gradient | 0.00 | 5 |
| | 10.00 | 25 |
| | 15.00 | 45 |
| | 20.00 | 90 |
| | 21.00 | 5 |
| Flow Rate | 1 mL/min | |
| Wave length | UV at 240nm | |
| Injection Volume | 10 μL | |
| Run time | 25 min | |
| Column Temperature | 35° C. | |
| Sample temperature | Ambient | |
| Diluent | water/acetonitrile (3/1 v/v) | |
| Target analytical concentration | ~0.1 mg/ml | |

Example 1—Synthesis of (4-(2-fluoro-4-(1l-methyl-1H-benzo[d]imidazol-5-yl)benzoyl) piperazin-1-yl)(1-hydroxycyclopropyl)methanone The synthesis of (4-(2-fluoro-4-(1-methyl-1H-benzo[d]imidazol-5-yl) benzoyl)piperazin-1-yl)(1-hydroxycyclopropyl)methanone ("Compound 1") was previously reported in PCT Application Publication No. WO 2014/164749. Compound 1 may be prepared as shown below:

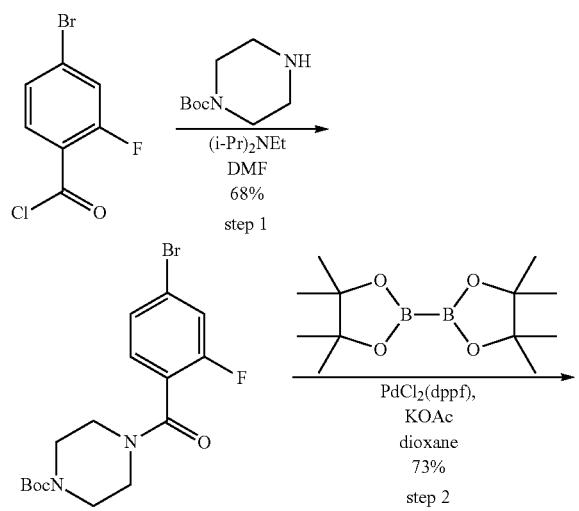

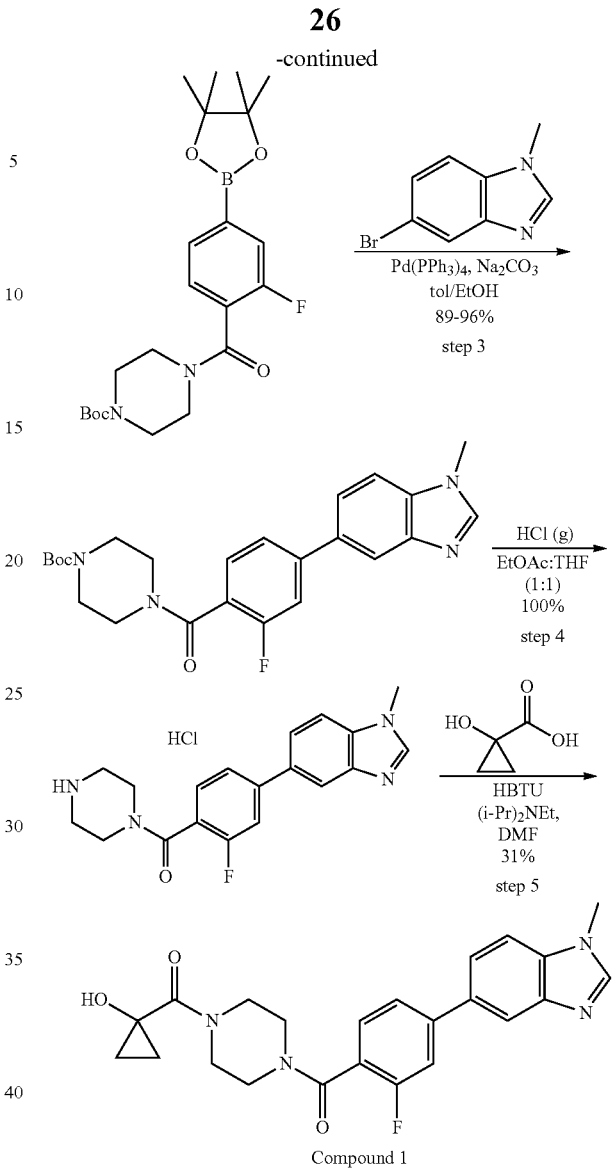

Compound 1

Step 1. tert-butyl 4-(4-bromo-2-fluorobenzoyl)piperazine-1-carboxylate

A 5 L multi-neck round bottom flask fitted with nitrogen inlet and overhead stirring was charged with 4-bromo-2-fluorobenzoyl chloride (100 g, 421 mmol), tert-butyl piperazine-1-carboxylate (78 g, 421 mmol), dimethylformamide (DMF) (750 mL), and diisopropylethylamine ((i-Pr)$_2$NEt; DIEA) (221 mL, 1263 mmol). The mixture was stirred at room temperature (rt) and monitored by liquid chromatography/mass spectrometry (LC/MS) for completion. Upon completion (ca. 2 hours) 0.2 M HCl (300 mL) was slowly added while maintaining internal temperature below 35° C. The heterogeneous mixture was stirred at rt for 3 hours, and then the solids were isolated by filtration. The reaction vessel and solids were washed with water (300 mL) and the solids were dried under house vacuum (17 torr) to afford tert-butyl 4-(4-bromo-2-fluorobenzoyl) piperazine-1-carboxylate (151 g, 93% yield) as an off white solid.

Step 2. (4-(4-(tert-butoxycarbonyl)piperazine-1-carbonyl)-3-fluorophenyl)boronic acid A 5 L multi-neck round bottom flask fitted with nitrogen inlet, overhead stirring, thermocouple and condenser was charged with tert-butyl 4-(4-bromo-2-fluorobenzoyl)piperazine-1-carboxylate (125 g, 323 mmol), potassium acetate (79 g, 807 mmol), 4,4,4',4',5,5,5',5'-octamethyl-2,2'-bi(1,3,2-dioxaborolane) (102 g, 403 mmol), 2-methyl tetrahydrofuran (1250 mL). The mixture was sparged with nitrogen and then PdCl$_2$(dppf) was added (2.362 g, 3.23 mmol). The mixture was heated to 75° C. and monitored for completion by LC/MS. Upon completion (about 24 hours) the mixture was cooled to rt and diluted with water (1250 mL). The bi-phasic mixture was filtered through celite, and the reaction vessel and celite were washed with fresh 2-methyltetrahydrofuran (250 mL). The phases were separated and the organic phase was washed with water (1250 mL). The organic phase was diluted with 1M NaOH (1250 mL) and the phases separated. The aqueous (product containing) phase was diluted with fresh 2-methyltetrahydrofuran (1400 mL), and the pH was adjusted to 1.0 with 6 M HCl. The phases were separated, and the organic (product containing) phase was filtered through celite and added to a 5 L multi-neck round bottom flask fitted with nitrogen inlet and overhead stirring, containing water (1400 mL) and sodium periodate (110 g, 516 mmol). The mixture was stirred for 1 hour, followed by the addition of 1 M HCl (980 ml). The mixture was stirred at rt and monitored for completion by LC/MS. Upon completion (about 18 hours) the phases were separated, and the organic phase was washed with 20 wt % aqueous Na$_2$S$_2$O$_3$ (500 mL), water (500 mL), and brine (500 mL). The organic phase was dried with magnesium sulfate, filtered, and the solids washed with fresh 2-methyltetrahydrofuran (200 mL). The filtrate was concentrated to dryness under reduced pressure to afford (4-(4-(tert-butoxycarbonyl)piperazine-1-carbonyl)-3-fluorophenyl)boronic acid (100.22 g, 88% yield) as a tan solid.

Step 3. tert-butyl 4-(2-fluoro-4-(1-methyl-1H-benzo[d]imidazol-5-yl)benzoyl)piperazine-1-carboxylate Into a 100-mL round-bottom flask purged and maintained with an inert atmosphere of nitrogen, was placed a solution of (4-(4-(tert-butoxycarbonyl)piperazine-1-carbonyl)-3L-fluorophenyl) boronic acid (620 mg, 1.42 mmol, 1.00 equiv), toluene (10 mL), 5-bromo-1-methyl-1H-1,3-benzodiazole (300 mg, 1.42 mmol, 1.00 equiv), Pd(PPh$_3$)$_4$ (198 mg, 0.17 mmol, 0.12 equiv), sodium carbonate (2 M, 5 mL), and ethanol (1.4 mL). The resulting mixture was stirred overnight at 95° C. After cooling to room temperature, the mixture was diluted with 20 mL H$_2$O, extracted with 3×30 mL of ethyl acetate. All the organic layers were combined, dried over anhydrous sodium sulfate, and concentrated under vacuum. The residue was loaded onto a silica gel column with dichloromethane/methanol (95:5). The collected fractions were combined and concentrated under vacuum. This resulted in 600 mg (96%) of tert-butyl 4-(2-fluoro-4-(1-methyl-1H-benzo[d]imidazol-5-yl) benzoyl) piperazine-1-carboxylate as a yellow solid. LC-MS (ES, m/z): 439 [M+H]$^+$.

Step 4. (2-fluoro-4-(1-methyl-1H-benzo[d]imidazol-5-yl) phenyl)(piperazin-1-yl)methanone (hydrochloride salt)

Into a 100-mL round-bottom flask, was placed a solution of tert-butyl 4-(2-fluoro-4-(1-methyl-1H-benzo[d]imidazol-5-yl) benzoyl)piperazine-1-carboxylate (600 mg, 1.37 mmol, 1.00 equiv) in ethyl acetate (EA)/THF(1:1, 20 mL). Hydrogen chloride gas was then bubbled into the reaction mixture. The solution was stirred for 30 min at room temperature. The solids were collected by filtration and dried under reduced pressure. This resulted in 460 mg (100%) of (2-fluoro-4-(1-methyl-1H-benzo[d]imidazol-5-yl) phenyl) (piperazin-1-yl)methanone (hydrochloride salt) as an off-white solid. LC-MS (ES, m/z): 339 [M+H]$^+$.

Step 5. (4-(2-fluoro-4-(1-methyl-1H-benzo[d]imidazol-5-yl)benzoyl)piperazin-1-yl)(1-hydroxycyclopropyl)methanone Into a 100-mL round-bottom flask, was placed a solution of (2-fluoro-4L-(1-methyl-1H-benzo[d]imidazol-5-yl) phenyl)(piperazin-1-yl)methanone (hydrochloride salt) (398 mg, 1.18 mmol, 1.00 equiv) in N,N-dimethylformamide (20 mL), 1-hydroxycyclopropane-1-carboxylic acid (120 mg, 1.18 mmol, 1.00 equiv), HBTU (669 mg, 1.76 mmol, 1.50 equiv), and DIEA (608 mg, 4.70 mmol, 4.00 equiv). The resulting mixture was stirred overnight at room temperature. The solution was diluted with 30 mL of EA, washed with 3>30 mL H$_2$O. The organic phase was dried over anhydrous sodium sulfate and concentrated under vacuum. The residue was loaded onto a silica gel column with EA/petroleum ether (0:100-100:0). The collected fractions were combined and concentrated under vacuum to dryness. This resulted in 152.8 mg (31%) of (4-(2-fluoro-4-(1-methyl-1H-benzo[d] imidazol-5-yl) benzoyl)piperazin-1-yl)(1-hydroxycyclopropyl)methanone as a white solid. LC-MS: (ES, m/z): 423[M+H]$^+$. $^1$H-NMR: (CD$_3$OD, 300 MHz): δ8.20 (s, 1H), 7.96 (s, 1H), 7.68-7.63 (m, 3H), 7.59-7.50 (m, 2H), 3.95-3.72 (m, 9H), 3.50 (s, 2H), 1.10-1.06 (m, 2H), 0.93L-0.89 (m, 2H).

Example 2—Characterization of Solid Forms and Solid Form Mixtures of Compound 1 Mixture A Compound 1 Mixture A was prepared by replacing step 5 of Example 1 with step 6:

Step 6: (4-(2-fluoro-4-(1-methyl-1H-benzo[d]imidazol-5-yl)benzoyl)piperazin-1-yl)(1-hydroxycyclopropyl)methanone To a solution of 1-hydroxycyclopropane-1-carboxylic acid (30 g, 294 mmol) in DMF (900 mL) was added HBTU (36 g, 95.6 mmol), 5-[3-fluoro-4-[(piperazin-1-yl)carbonyl]phenyl]-1-methyl-1H-1, 3-benzodiazole hydrochloride (8.6 g, 22.9 mmol), and DIEA (52.8 mL, 319 mmol). The resulting solution was stirred for 18 hours at 20° C. The reaction mixture was poured into water (4 L) and then extracted with DCM (4×1.5 L). The organic layers were combined, dried over anhydrous sodium sulfate, filtered and concentrated under vacuum. The resulting crude product was purified by reversed phase chromatography (5% to 35% MeCN/water (containing 0.1% NH$_4$HCO$_3$) over 30 min). The fractions were collected and lyophilized. The product was further purified by recrystallization with MeOH/water (1:2) and dried under vacuum to afford 1-[(4-[[2-fluoro-4-(1-methyl-1H-1,3-benzodiazol-5-yl)phenyl]carbonyl]piperazin-1-yl) carbonyl]cyclopropan-1-ol as a white solid (11.46 g, 33.9%).The XRPD pattern of the crystalline Compound 1 Mixture A is depicted in FIG. 1, and the corresponding data is summarized below:

| 2 Theta | d-spacing (Å) |
| --- | --- |
| 7.9 | 11.1 |
| 9.6 | 9.3 |
| 10.1 | 8.7 |
| 10.7 | 8.3 |
| 12.6 | 7.0 |
| 13.4 | 6.6 |
| 13.9 | 6.4 |
| 14.3 | 6.2 |
| 15.4 | 5.7 |
| 16.3 | 5.4 |
| 16.8 | 5.3 |
| 17.4 | 5.1 |
| 18.5 | 4.8 |

| 2 Theta | d-spacing (Å) |
|---|---|
| 19.6 | 4.5 |
| 20.2 | 4.4 |
| 21.0 | 4.2 |
| 21.4 | 4.2 |
| 22.1 | 4.0 |
| 22.2 | 4.0 |
| 23.4 | 3.8 |
| 23.8 | 3.7 |
| 25.0 | 3.6 |
| 25.3 | 3.5 |
| 26.5 | 3.4 |
| 26.8 | 3.3 |
| 27.2 | 3.3 |
| 28.0 | 3.2 |
| 29.0 | 3.1 |
| 29.4 | 3.0 |
| 30.5 | 2.9 |
| 31.1 | 2.9 |
| 31.8 | 2.8 |
| 32.9 | 2.7 |
| 33.6 | 2.7 |
| 34.1 | 2.6 |
| 37.3 | 2.4 |
| 37.9 | 2.4 |

Figure 2:
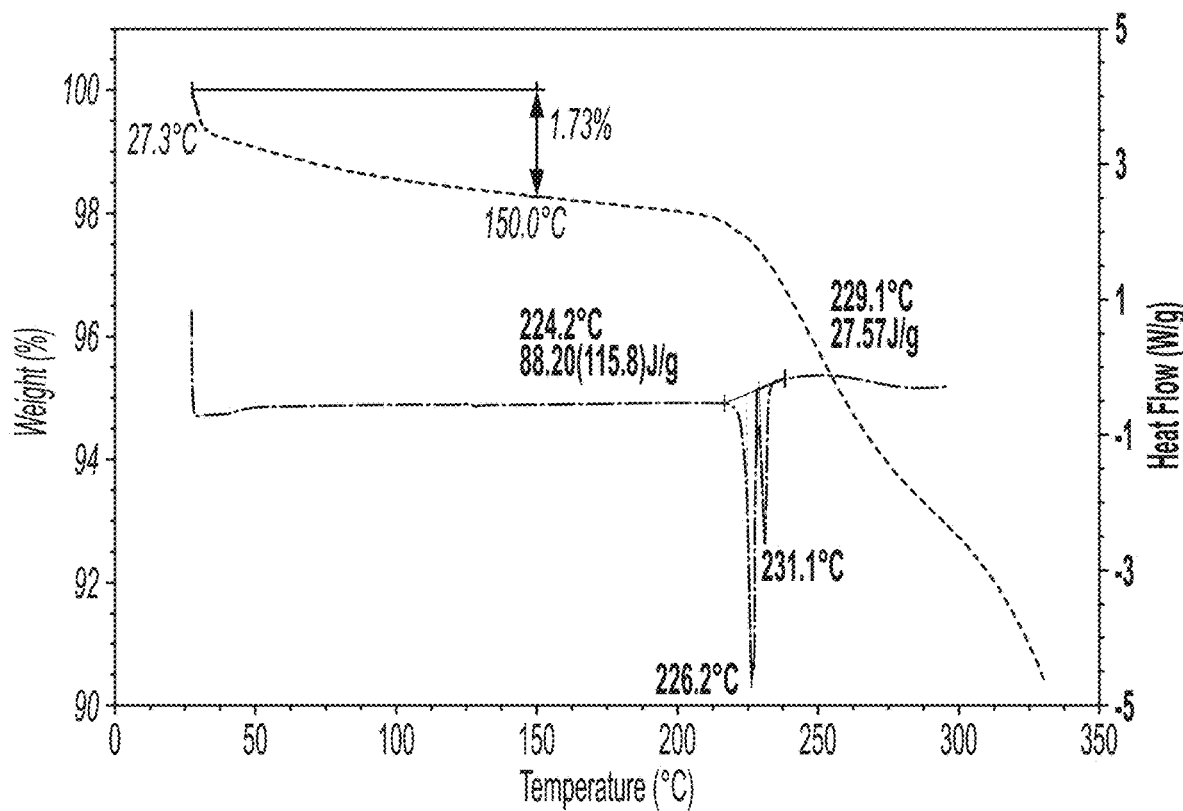
FIG. 2 is a thermogravimetric analysis (TGA) curve (upper curve) and a DSC thermogram (lower curve) for Compound 1 Mixture A.

As shown by TGA and DSC curves in FIG. 2, Mixture A showed a weight loss of 1.73% up to 150° C. and two endotherms at 226.2° C. and 229.1° C. (peak temperature) before decomposition.

Without wishing to be bound by any particular theory, Applicant has observed that Mixture A is an apparent mixture of two anhydrous forms: Form B and another solid form, as is apparent from the extra reflections in XRPD (FIG. 1) and additional endotherms in DSC (FIG. 2), compared with Form B alone.

Form B

Compound 1 Form B was prepared by one of the following procedures.

Procedure 1: Mixture A (0.10 g) was recrystallized from ACN-water (ca. 9:1, 10 volumes) to give Form B in 72% recovery.

Procedure 2: Form C (0.25 g) was slurried in heptane (40 volumes) at 100° C. for 7 hours, then cooled to room temperature and filtered to give Form B in 80% recovery, 98.95% purity.

Procedure 3: Form C (0.25 g) was slurried in IPA (40 volumes) at 80° C. for 7 hours, then cooled to room temperature and filtered to give Form B in 60% recovery, 99.02% purity.

Procedure 4: Form C (21 g) was slurried in heptane (10 volumes) at 105° C. for 5 hours, then cooled to room temperature, and filtered to give Form B in 91% recovery, 98.79% purity.

Procedure 5: Form C (30 g) was combined in IPA (15 volumes) and heated to reflux. IPA (7.5 volumes) was then distilled off. The resulting suspension was cooled to room temperature, filtered and dried at 50° C. and 80° C. to give 91% recovery, 99.27% purity.

Procedure 6: Form C (1.0 g) was dissolved in N-methyl-2-pyrrolidone (NMP) (9 volumes) at 50° C. The solution was cooled to room temperature and filtered. IPA (18 volumes) was added to the filtrate, then Form B seed crystals were added. The slurry was stirred at room temperature, filtered and dried to give 73% recovery, 99.48% purity.

Procedure 7: Form C (25 g) was slurried in ethanol (15 volumes) at 50° C. for 8 hours. The slurry was cooled to rt and filtered to give 99.51% purity.

Procedure 8: The final step of Example 1 was replaced with step 6:

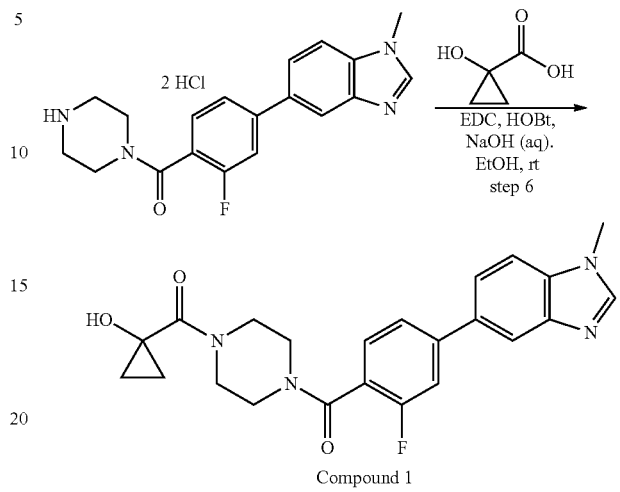

Compound 1

Step 6: (4-(2-fluoro-4-(1-methyl-1H-benzo[d]imidazol-5-yl)benzoyl)piperazin-1-yl)(1-hydroxycyclopropyl)methanone A 250-mL round-bottomed flask was charged with (2-fluoro-4-(1-methyl-1H-benzo[d]imidazol-5-yl)phenyl) (piperazin-1-yl)methanone (hydrochloride salt) (10. 36 g, 1.00 equiv), HOBt (861 mg, 1.30 equiv), and EtOH (40 mL). With moderate agitation, the suspension was charged with 3 M NaOH (aq) (19.0 mL, 2.35 equiv), and the reaction mixture was agitated at room temperature for 10 minutes. The reaction mixture was filter using a Buchner funnel to give a first solution. A separate 100-mL round-bottomed flask was charged with EDC·HCl (5.59 g, 1.2 equiv) and 25 mL EtOH. The resulting mixture was agitated at room temperature for 10 minutes, and then filtered using a Buchner funnel to give a second solution. To the first solution was added the second solution over the course of an hour. The reaction mixture was agitated at room temperature for about 7 hours. The reaction mixture was then added to water (250 mL) in portions over the course of an hour, and the resulting mixture was agitated for about 3 hours. The reaction mixture was filtered using a Buchner funnel and washed with water (100 mL) to give (4-(2-fluoro-4-(1-methyl-1H-benzo[d]imidazol-5-yl) benzoyl)piperazin-1-yl)(1-hydroxycyclopropyl) methanone in about 90% yield.

Figure 3:
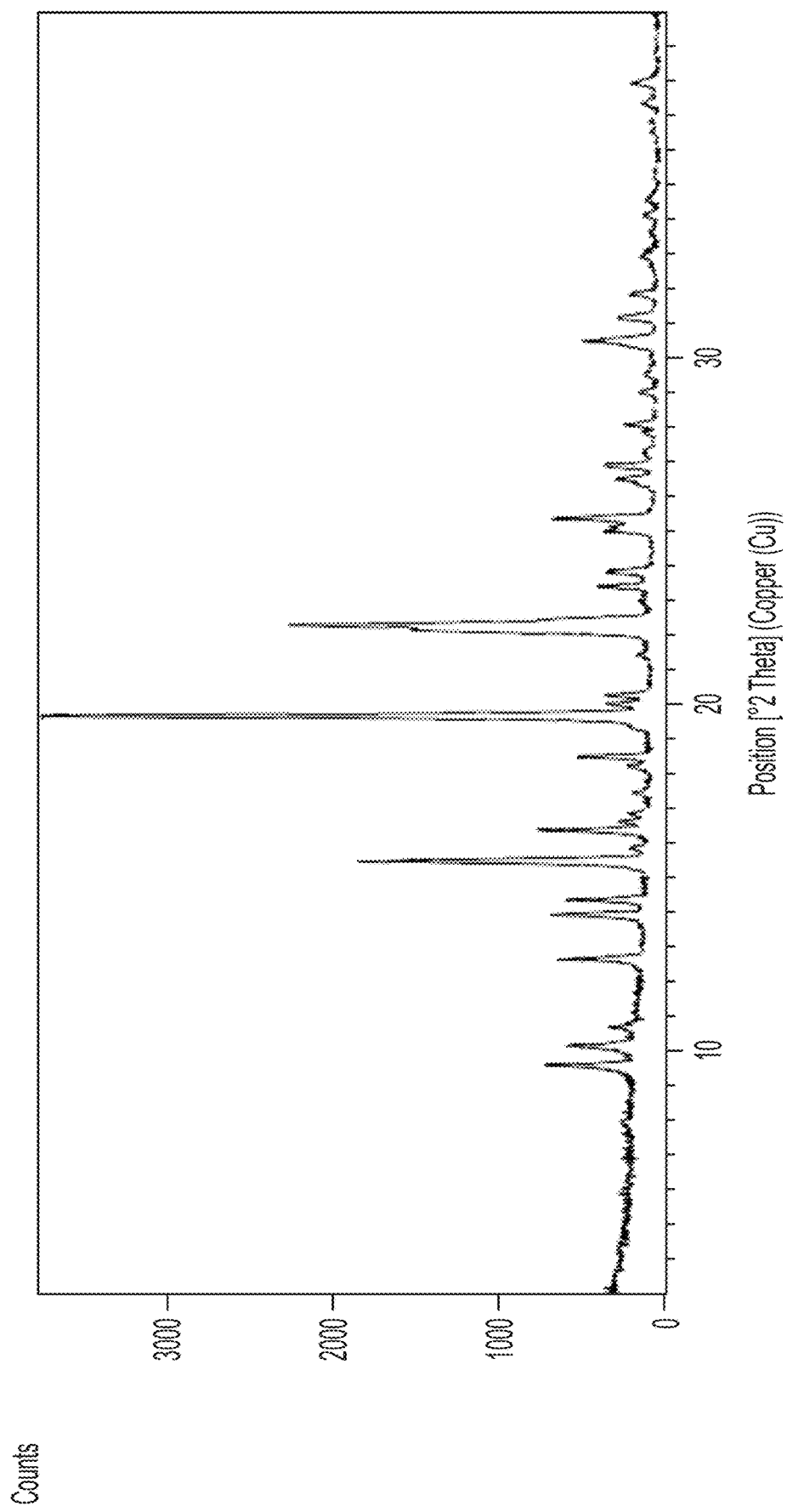
FIG. 3 depicts an XRPD pattern of Compound 1 Form B.

The XRPD pattern of the crystalline Compound 1 Form B is depicted in FIG. 3, and the corresponding data is summarized below:

| 2 Theta | d-spacing (Å) |
|---|---|
| 9.6 | 9.2 |
| 10.1 | 8.7 |
| 10.7 | 8.3 |
| 12.6 | 7.0 |
| 13.9 | 6.4 |
| 14.3 | 6.2 |
| 15.4 | 5.7 |
| 16.4 | 5.4 |
| 16.6 | 5.3 |
| 17.4 | 5.1 |
| 18.2 | 4.9 |
| 18.5 | 4.8 |
| 19.6 | 4.5 |

| 2 Theta | d-spacing (Å) |
|---|---|
| 20.2 | 4.4 |
| 22.1 | 4.0 |
| 22.3 | 4.0 |
| 23.4 | 3.8 |
| 23.8 | 3.7 |
| 25.0 | 3.6 |
| 25.3 | 3.5 |
| 26.5 | 3.4 |
| 26.9 | 3.3 |
| 28.0 | 3.2 |
| 29.0 | 3.1 |
| 29.5 | 3.0 |
| 30.5 | 2.9 |
| 31.1 | 2.9 |
| 31.8 | 2.8 |
| 32.9 | 2.7 |
| 34.1 | 2.6 |
| 37.3 | 2.4 |
| 37.9 | 2.4 |

Figure 4:
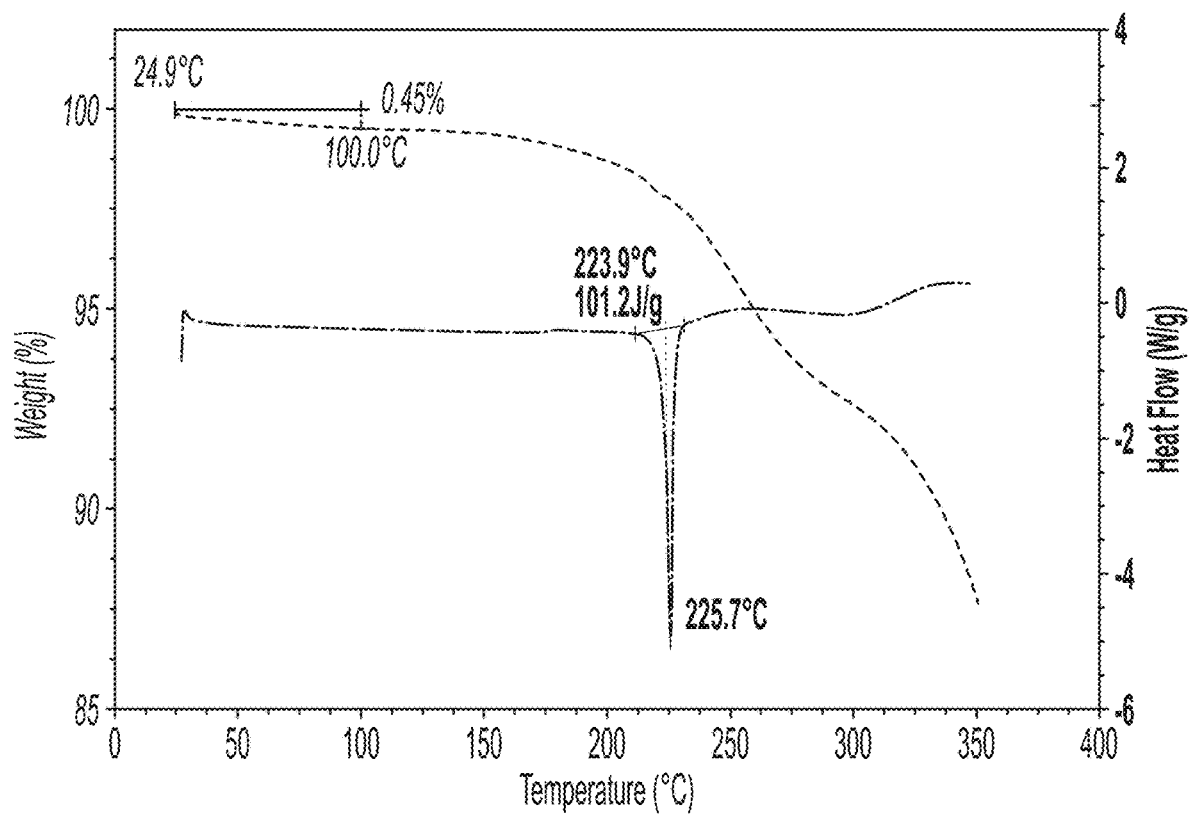
FIG. 4 is a TGA curve (upper curve) and a DSC thermogram (lower curve) for Compound 1 Form B.

As shown by TGA and DSC curves in FIG. 4, Form B showed a weight loss of 0.45% up to 100° C. and one endothermic peak at 223.9° C. (onset temperature); 225.7° C. (peak temperature) before decomposition.

Figure 5:
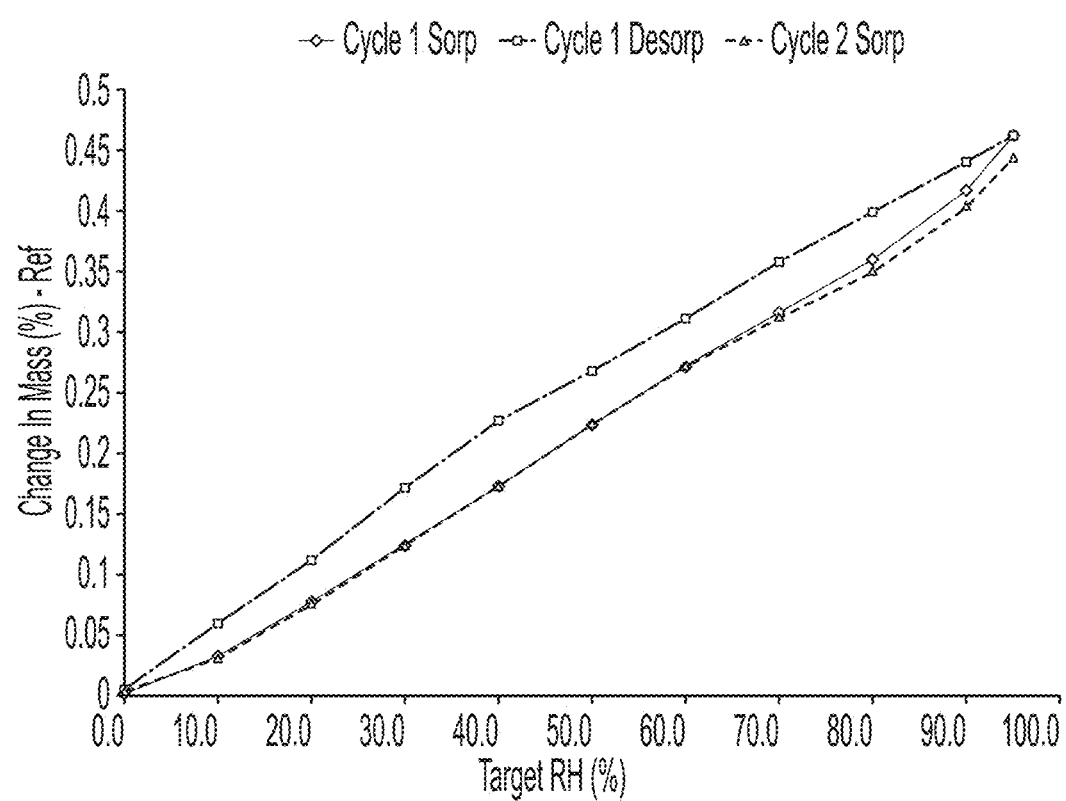
FIG. 5 depicts a Dynamic Vapor Sorption (DVS) plot of Compound 1 Form B.
Figure 6:
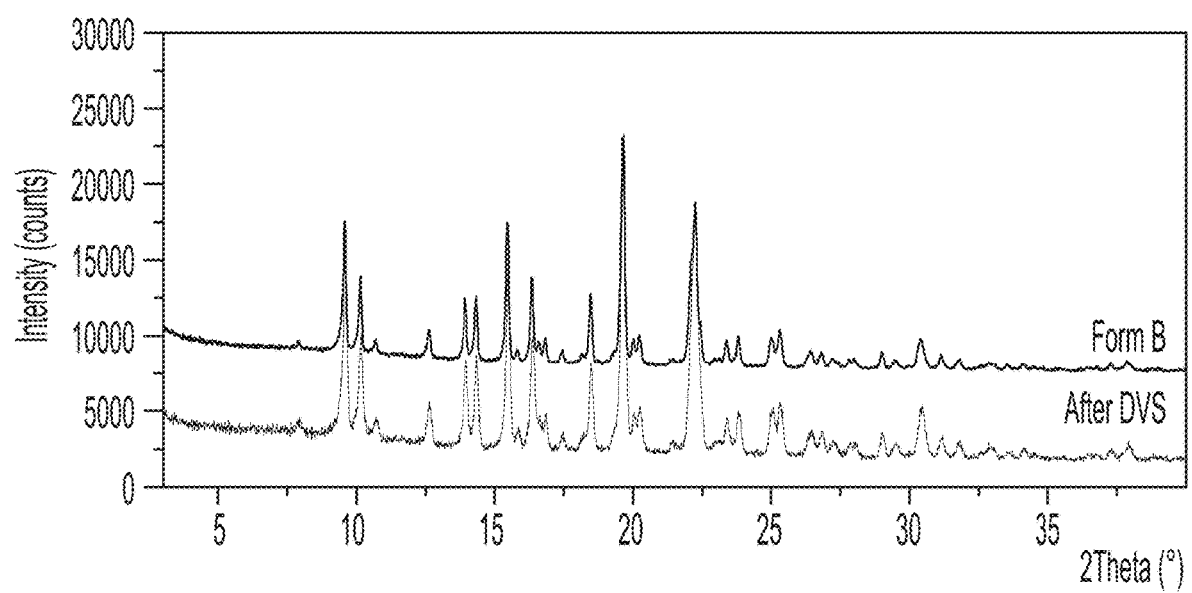
FIG. 6 depicts a series of XRPD patterns of Compound 1 Form B before and after DVS analysis.

DVS analysis was also conducted for Form B. As shown in FIG. 5, a mass change of 0.46 wt % was observed for Form B from 0% RH to 95% RH at 25° C. The sample was non-hygroscopic. As shown by XRPD in FIG. 6, no form change was observed for Form B before and after DVS.

A study was conducted on a sample of Compound 1 (Form B) where samples were exposed (open) to a range of elevated temperatures (50-80° C.) and controlled relative humidity (RH) (0-80% RH). Compound 1 exhibits good chemical stability, and the estimated shelf life is greater than 5 years at 25° C./60% RH.

Form C

Compound 1 Form C was prepared by replacing step 5 of Example 1 with either step 7a or step 7b:

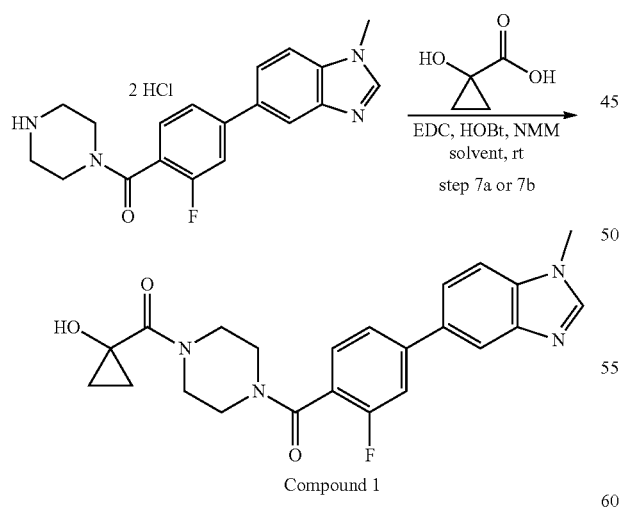

Compound 1

Step 7a: (4-(2-fluoro-4-(1-methyl-1H-benzo[d]imidazol-5-yl)benzoyl)piperazin-1-yl)(1-hydroxycyclopropyl)methanone To a 2-L, three-necked, round-bottomed flask fitted with a nitrogen inlet, and overhead stirring was added (2-fluoro-4-(1-methyl-1H-benzo[d]imidazol-5-yl)phenyl)(piperazin-1-yl)methanone dihydrochloride (139.21 g, 338 mmol), 1-hydroxycyclopropanecarboxylic acid (44.9 g, 440 mmol), 1-hydroxybenzotriazole hydrate (10.37 g, 67.7 mmol), N-(3-Dimethylaminopropyl)-N'-ethylcarbodiimide hydrochloride (84 g, 440 mmol), dimethyl sulfoxide (DMSO) (700 mL), and 4-methylmorpholine (167 mL, 1523 mmol). The mixture stirred at rt and monitored for completion by LC/MS. Upon reaction completion (ca. 18 hours) the mixture was added to a 5-L, three-necked, round-bottomed flask fitted with a nitrogen inlet and overhead stirring containing water (2800 mL). The mixture was granulated for 24 hours and then filtered. The isolated solids were then stirred in water (1200 mL) at rt for 4 hours, filtered, and washed with water (300 mL). The solids were dried on filter under a nitrogen atmosphere followed by house vacuum (ca. 17 torr) to afford (4-(2-fluoro-4-(1-methyl-1H-benzo[d]imidazol-5-yl) benzoyl)piperazin-1-yl)(1-hydroxycyclopropyl)methanone (118.7 g, 83% yield) as a white solid.

Step 7b: (4-(2-fluoro-4-(1-methyl-1H-benzo[d]imidazol-5-yl) benzoyl)piperazin-1-yl)(1-hydroxycyclopropyl)methanone To a 50-mL, round-bottomed flask fitted with a nitrogen inlet and magnetic stir bar was added (2-fluoro-4-(1-methyl-1H-benzo[d]imidazol-5-yl)phenyl)(piperazin-1-yl)methanone dihydrochloride (3.0 g, 7.29 mmol), 1-hydroxycyclopropane-1-carboxylic acid (0.968 g, 9.48 mmol), 1-hydroxybenzotriazole hydrate (0.223 g, 1.459 mmol), N-(3-Dimethylaminopropyl)-N'-ethylcarbodiimide hydrochloride (1.818 g, 9.48 mmol), N-Methyl-2-pyrrolidinone (NMP) (15 mL), and 4-methylmorpholine (3.6 mL, 32.8 mmol). The mixture was stirred at rt and monitored for completion by LC/MS. Upon reaction completion (ca. 3 hours) the mixture was added to water (50 mL) and the resulting mixture stirred at rt overnight. The mixture was then filtered, and the solids washed with water (10 mL). The solids were dried on house vacuum (ca. 17 torr) to afford (4-(2-fluoro-4-(1-methyl-1H-benzo[d]imidazol-5-yl)benzoyl)piperazin-1-yl)(1-hydroxycyclopropyl)methanone (2.62 g, 85% yield) as a white solid containing 1.43 wt. % N-Methyl-2-pyrrolidinone.

Figure 7:
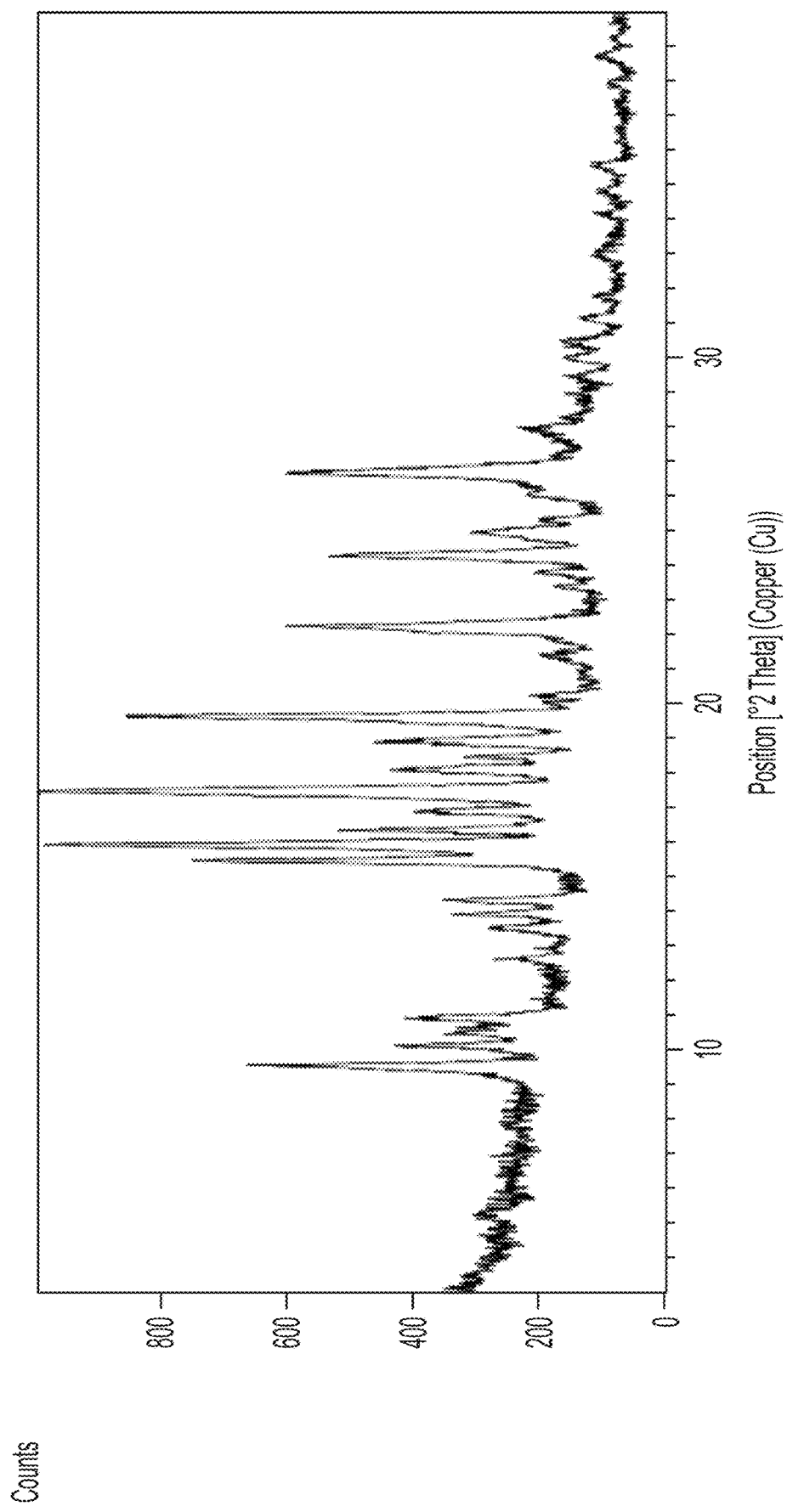
FIG. 7 depicts an XRPD pattern of Compound 1 Form C.

The XRPD pattern of the crystalline Compound 1 Form C is depicted in FIG. 7, and the corresponding data is summarized below:

| 2 Theta | d-spacing (Å) |
|---|---|
| 9.6 | 9.3 |
| 10.1 | 8.8 |
| 10.9 | 8.1 |
| 13.5 | 6.6 |
| 13.9 | 6.4 |
| 14.3 | 6.2 |
| 15.5 | 5.7 |
| 15.9 | 5.6 |
| 16.3 | 5.4 |
| 16.8 | 5.3 |
| 17.5 | 5.1 |
| 18.1 | 4.9 |
| 18.4 | 4.8 |
| 18.9 | 4.7 |
| 19.6 | 4.5 |
| 22.2 | 4.0 |
| 24.2 | 3.7 |
| 24.9 | 3.6 |
| 26.6 | 3.3 |
| 27.9 | 3.2 |
| 30.5 | 2.9 |

-continued

| 2 Theta | d-spacing (Å) |
|---|---|
| 31.1 | 2.9 |
| 35.5 | 2.5 |
| 38.7 | 2.3 |

Figure 8:
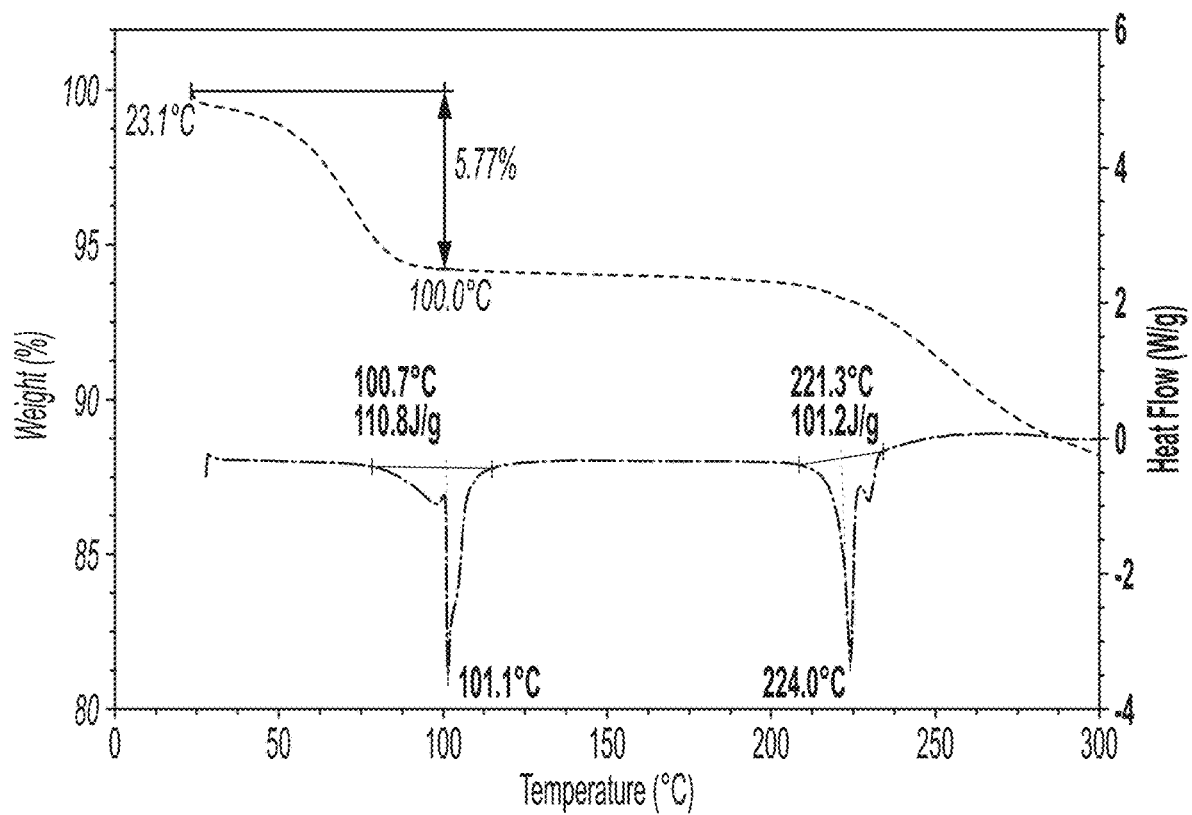
FIG. 8 is a TGA curve (upper curve) and a DSC thermogram (lower curve) for Compound 1 Form C.

As shown by TGA and DSC curves in FIG. 8, Form C showed a weight loss of 5.77% up to 100° C. and two endotherms at 101.1° C. and 224.0° C. before decomposition.

Form X

Compound 1 Form X was prepared by the following procedure:

To a 50-mL, round-bottomed flask fitted with a nitrogen inlet and magnetic stir bar was added (4-(2-fluoro-4-(1-methyl-1H-benzo[d]imidazol-5-yl)benzoyl)piperazin-1-yl)(1-hydroxycyclopropyl)methanone (5.0 g, 11.84 mmol) and acetonitrile (15 mL). To the mixture was added 1M HCl in water (15.00 mL, 15.00 mmol) with stirring. The homogeneous mixture was stirred at rt for 2 hours and then filtered through a fritted filter to remove insoluble material. The filtrate was cooled to 0° C. and 1M NaOH (15.00 mL, 15.00 mmol) was added at such a rate so as to maintain the temperature below 10° C. The mixture was stirred cold for 10 minutes and then allowed to warm to rt, during which time solids began to precipitate. The mixture was allowed to granulate overnight at rt. After overnight stirring (18 hours) the mixture was filtered, and the solids washed with water (15 mL). The material was dried on the filter under a nitrogen atmosphere followed by house vacuum (ca. 17 torr) to afford (4-(2-fluoro-4-(1-methyl-1H-benzo[d]imidazol-5-yl) benzoyl)piperazin-1-yl)(1-hydroxycyclopropyl)methanone (4.47 g, 89% yield) as a white solid.

Figure 9:
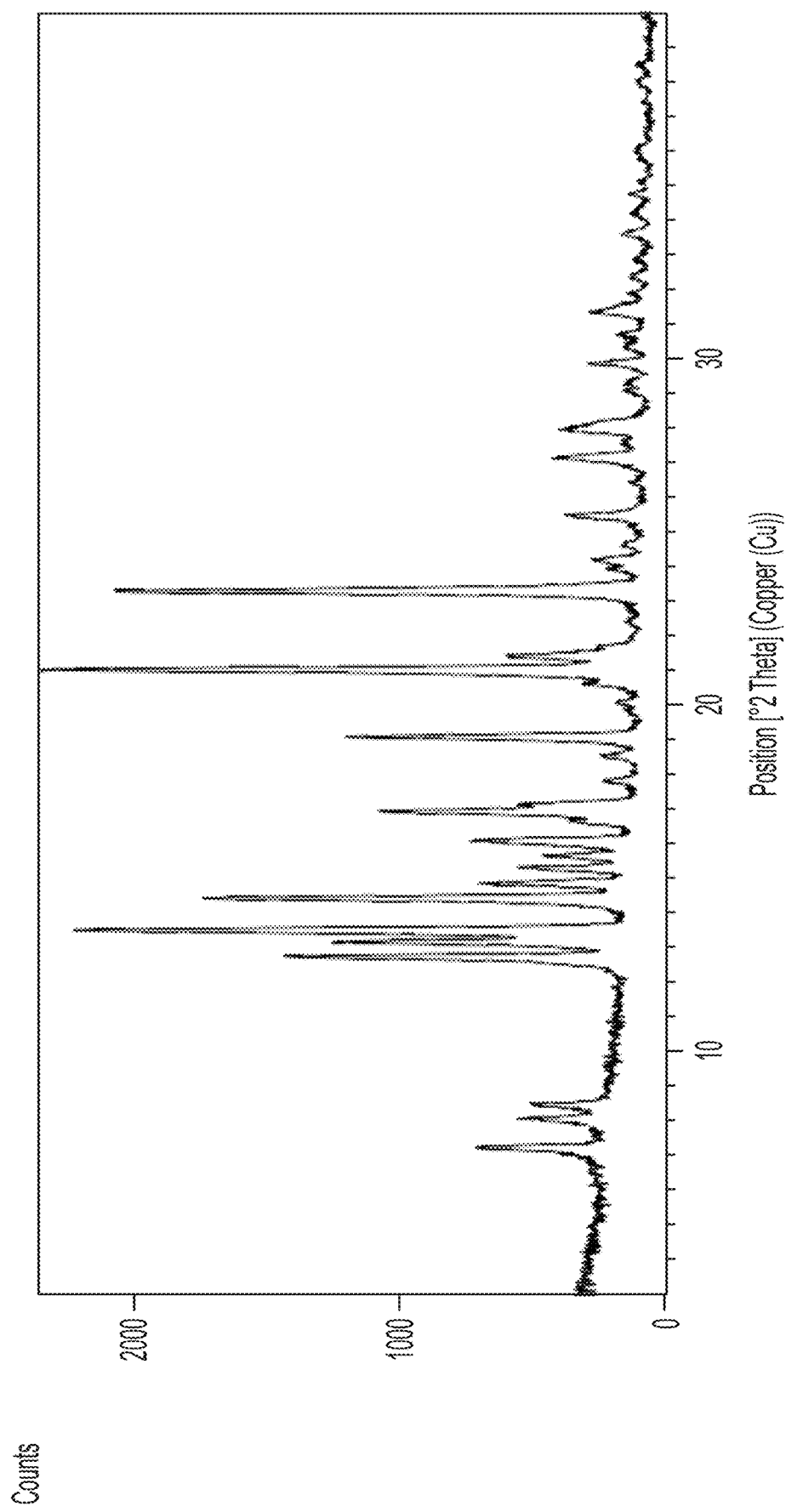
FIG. 9 depicts an XRPD pattern of Compound 1 Form X.

The XRPD pattern of the crystalline Compound 1 Form X is depicted in FIG. 9, and the corresponding data is summarized below:

| 2 Theta | d-spacing (Å) |
|---|---|
| 7.2 | 12.2 |
| 8.1 | 11.0 |
| 8.5 | 10.4 |
| 12.7 | 7.0 |
| 13.1 | 6.7 |
| 13.5 | 6.6 |
| 14.4 | 6.1 |
| 14.9 | 6.0 |
| 15.3 | 5.8 |
| 15.6 | 5.7 |
| 16.1 | 5.5 |
| 16.9 | 5.2 |
| 17.1 | 5.2 |
| 17.8 | 5.0 |
| 18.5 | 4.8 |
| 19.1 | 4.7 |
| 21.0 | 4.2 |
| 21.4 | 4.2 |
| 23.3 | 3.8 |
| 24.2 | 3.7 |
| 25.5 | 3.5 |
| 27.1 | 3.3 |
| 27.9 | 3.2 |
| 29.1 | 3.1 |
| 29.8 | 3.0 |
| 30.6 | 2.9 |
| 31.2 | 2.9 |
| 32.3 | 2.8 |
| 33.6 | 2.7 |
| 35.9 | 2.5 |
| 38.1 | 2.4 |

Figure 10:
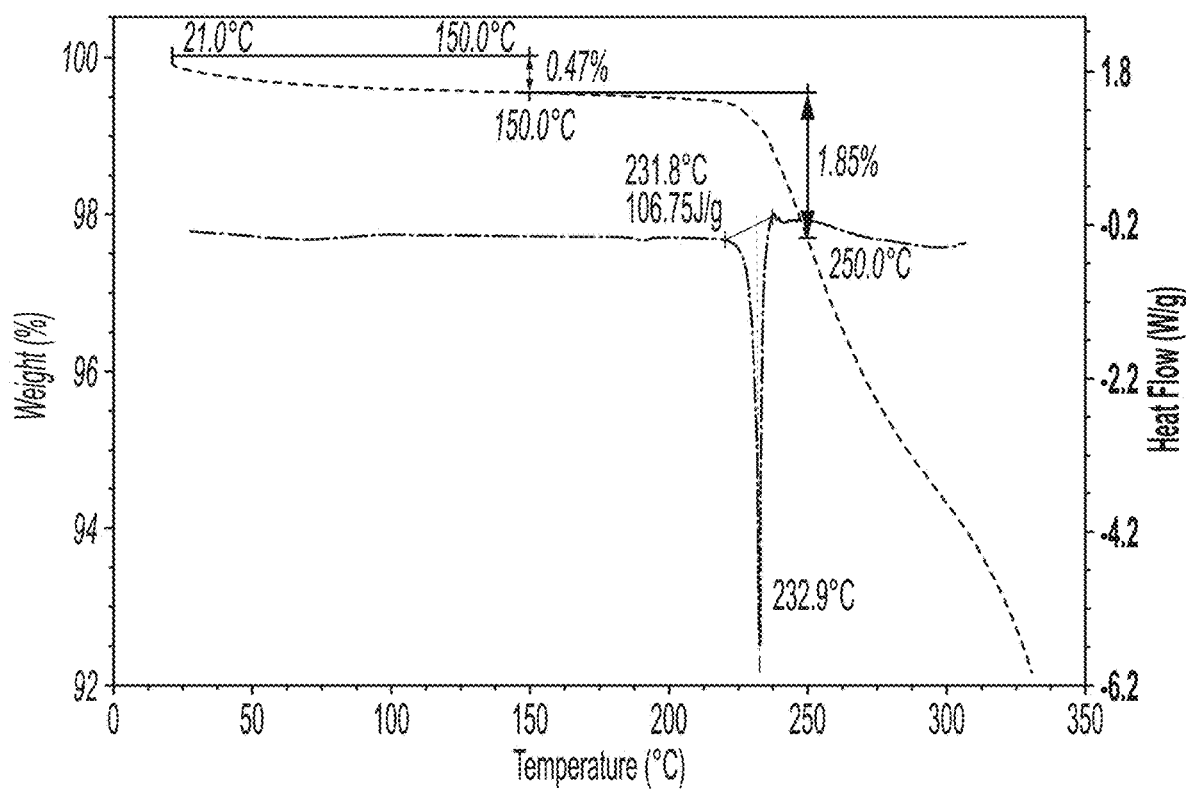
FIG. 10 is a TGA curve (upper curve) and a DSC thermogram (lower curve) for Compound 1 Form X.

As shown by TGA and DSC curves in FIG. 10, Form X showed a weight loss of 0.47% up to 150° C. and one endotherm at 232.9° C. (peak temperature) before decomposition.

Form Z

Compound 1 Form Z was prepared by dissolving Compound 1 Mixture A in chloroform ($CHCl_3$), followed by slow evaporation of the chloroform.

Figure 11:
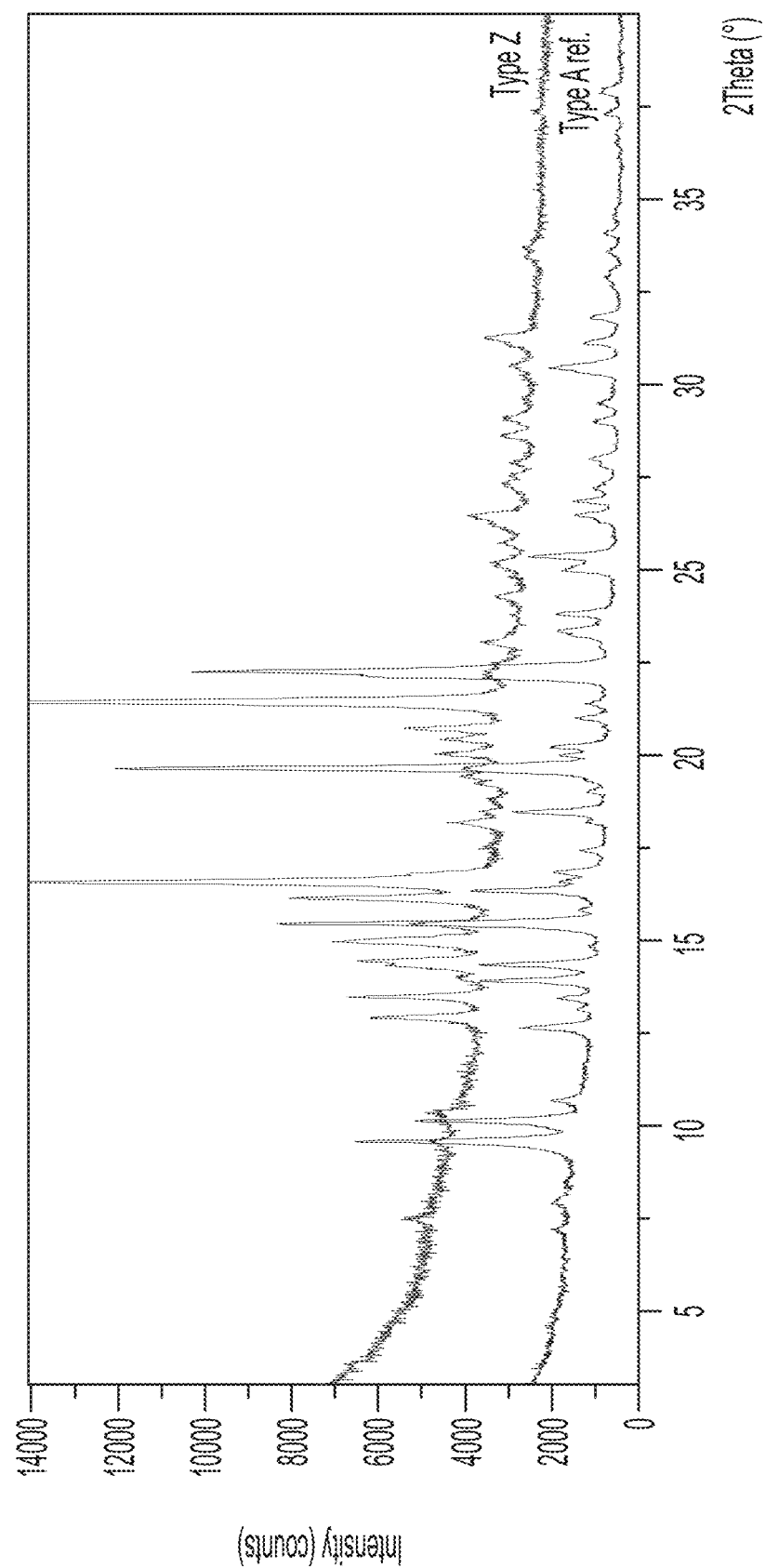
FIG. 11 depicts an XRPD pattern of Compound 1 Form Z, along with a reference pattern of Compound 1 Mixture A.

The XRPD pattern of the crystalline Compound 1 Form Z is depicted in FIG. 11, along with a reference pattern of Compound 1 Mixture A.

Figure 12:
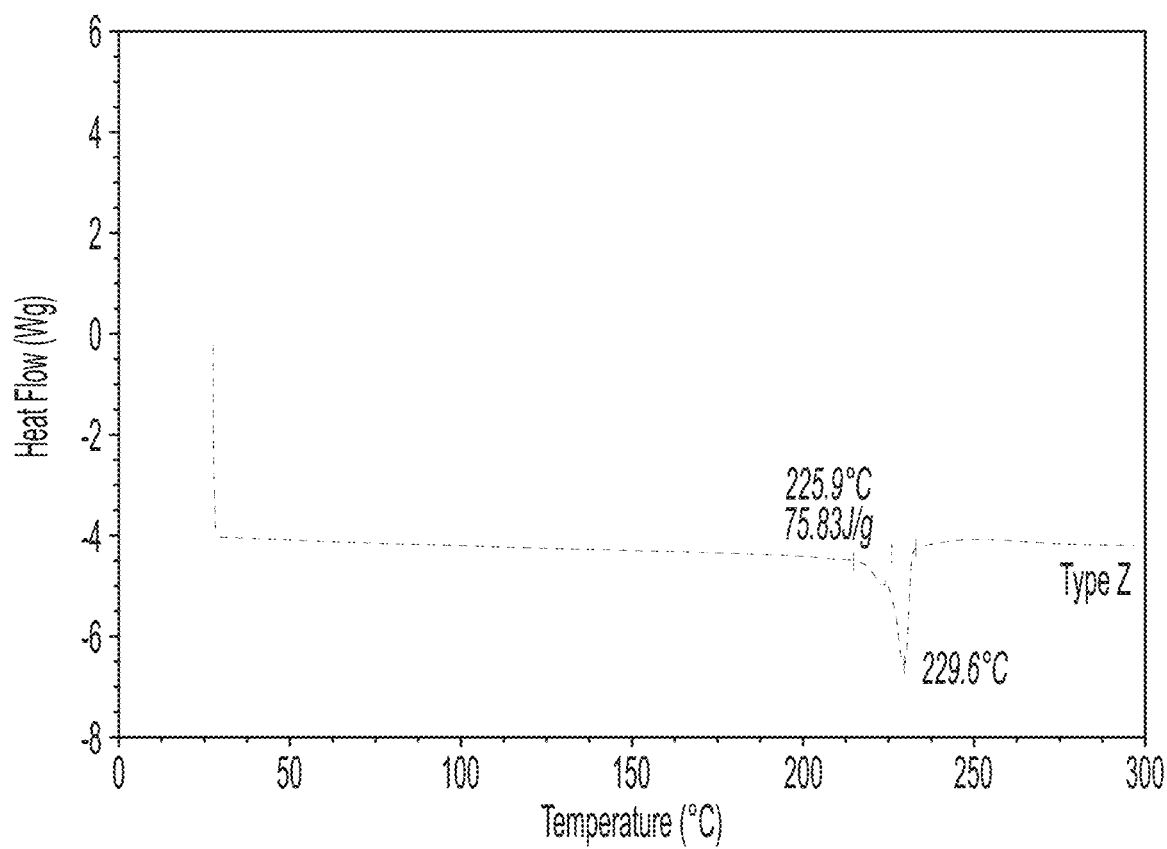
FIG. 12 is a DSC thermogram for Compound 1 Form Z.

As shown by the DSC curve in FIG. 12, Form Z showed one endothermic peak at 225.9° C. (onset temperature) and 229.6° C. (peak temperature) before decomposition.

Example 3—Stability Evaluation of Mixture A, Form B, and Form X

Slurry experiments with Mixture A were performed in two non-solvating solvents, EtOAc and ACN, at room temperature (RT) and 50° C. in order to evaluate the stability of Form B and Form X, which are two possible component forms of Mixture A. Mixture A was suspended in either EtOAc or ACN and stirred at either RT or 50° C., as indicated in Table 6, for 4 days. The solids collected were analyzed by XRPD to confirm the form change.

Figure 13:
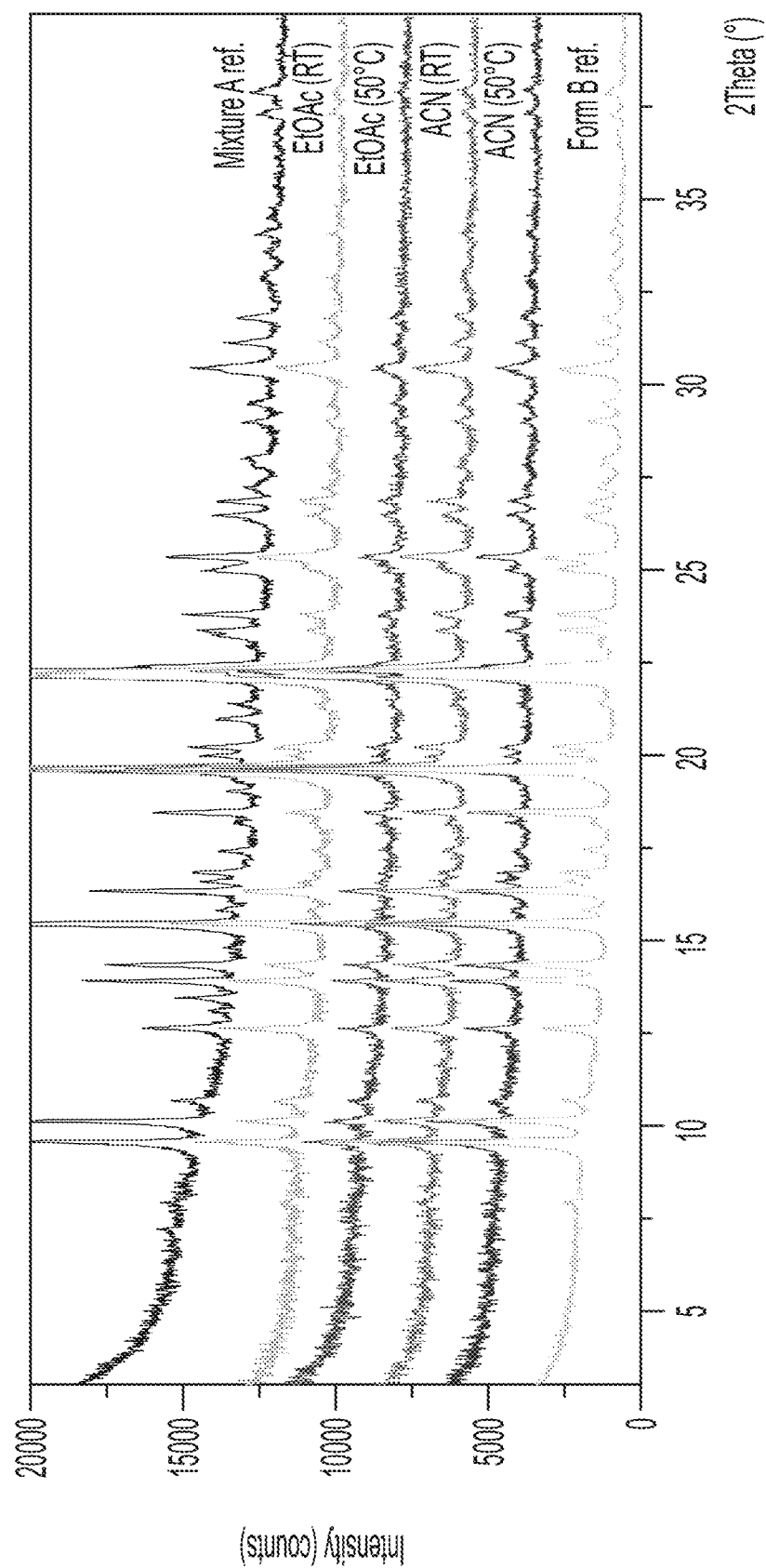
FIG. 13 depicts a series of XRPD patterns from the results of a stability evaluation of Compound 1 Mixture A, Form B, and Form X.

As summarized in Table 6 and FIG. 13, the solids from the slurries converted to Form B completely.

TABLE 6

| Solvent | Temperature | Results |
|---|---|---|
| EtOAc | RT | Form B |
| ACN | RT | Form B |
| EtOAc | 50° C. | Form B |
| ACN | 50° C. | Form B |

Example 4—Stability Evaluation of Form B and Form C

To evaluate the stability relationship between the hydrate Form C and the most stable anhydrate Form B, slurry competition experiments with Form B and Form C were conducted in different water activity ($A_w$) at RT. Form C was dissolved in three solvent mixtures (see Table 7) to get saturated solutions. Similar mass of Form B and Form C were added into the saturated solutions. The suspensions obtained were stirred at room temperature for 4 days and the solids collected were analyzed with XRPD.

Figure 14:
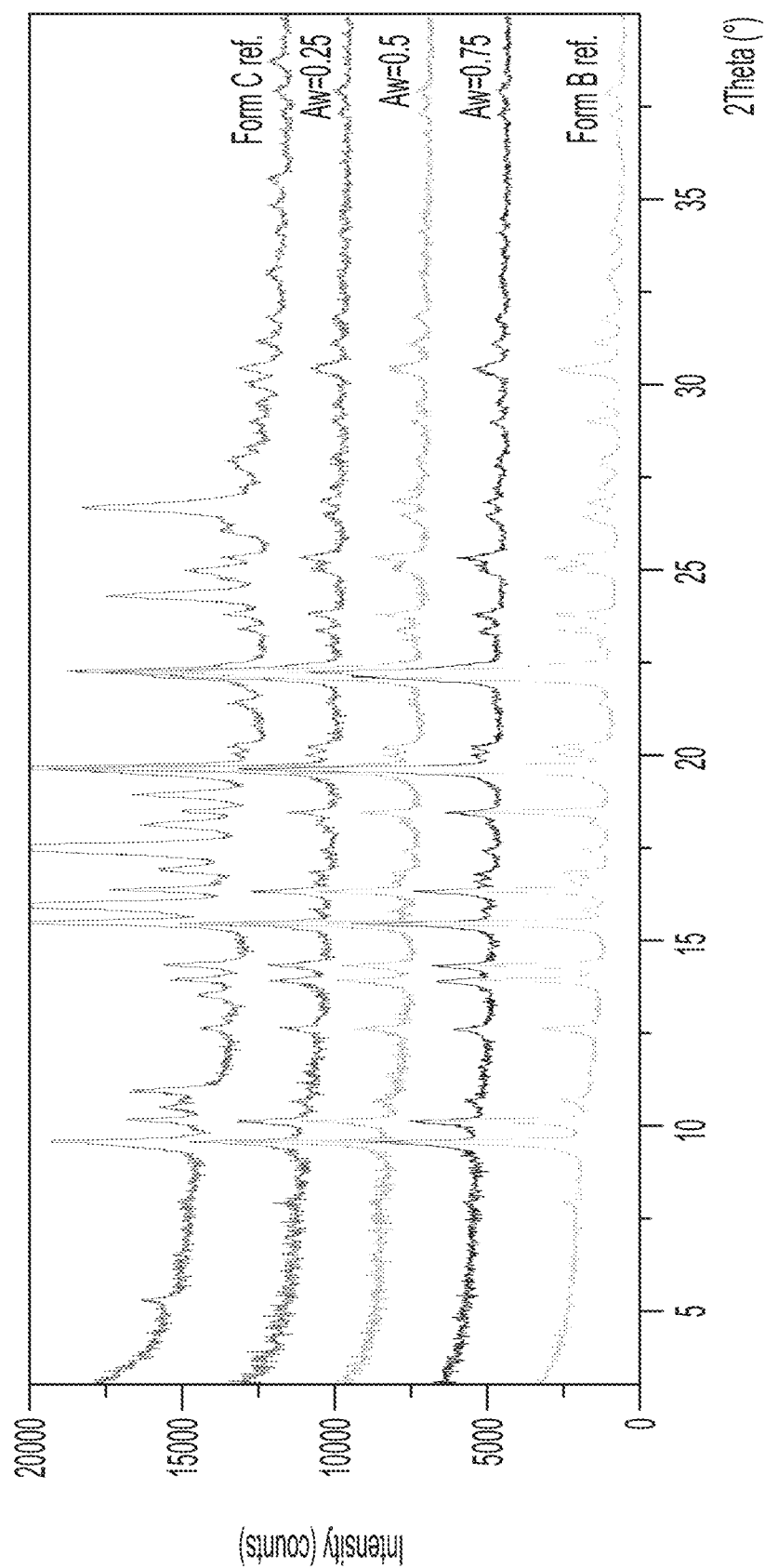
FIG. 14 depicts a series of XRPD patterns from the results of a stability evaluation of Compound 1 Form B and Form C.

As summarized in Table 7 and FIG. 14, the mixtures of Form B and Form C all converted completely to Form B.

TABLE 7

| Solvent | $A_w$ | Temp. | Results |
|---|---|---|---|
| $H_2O$/MeOH (85:915 v/v) | 0.25 | RT | Form B |
| $H_2O$/MeOH (225:775 v/v) | 0.5 | RT | Form B |
| $H_2O$/MeOH (494:506 v/v) | 0.75 | 50° C. | Form B |

Figure 15:
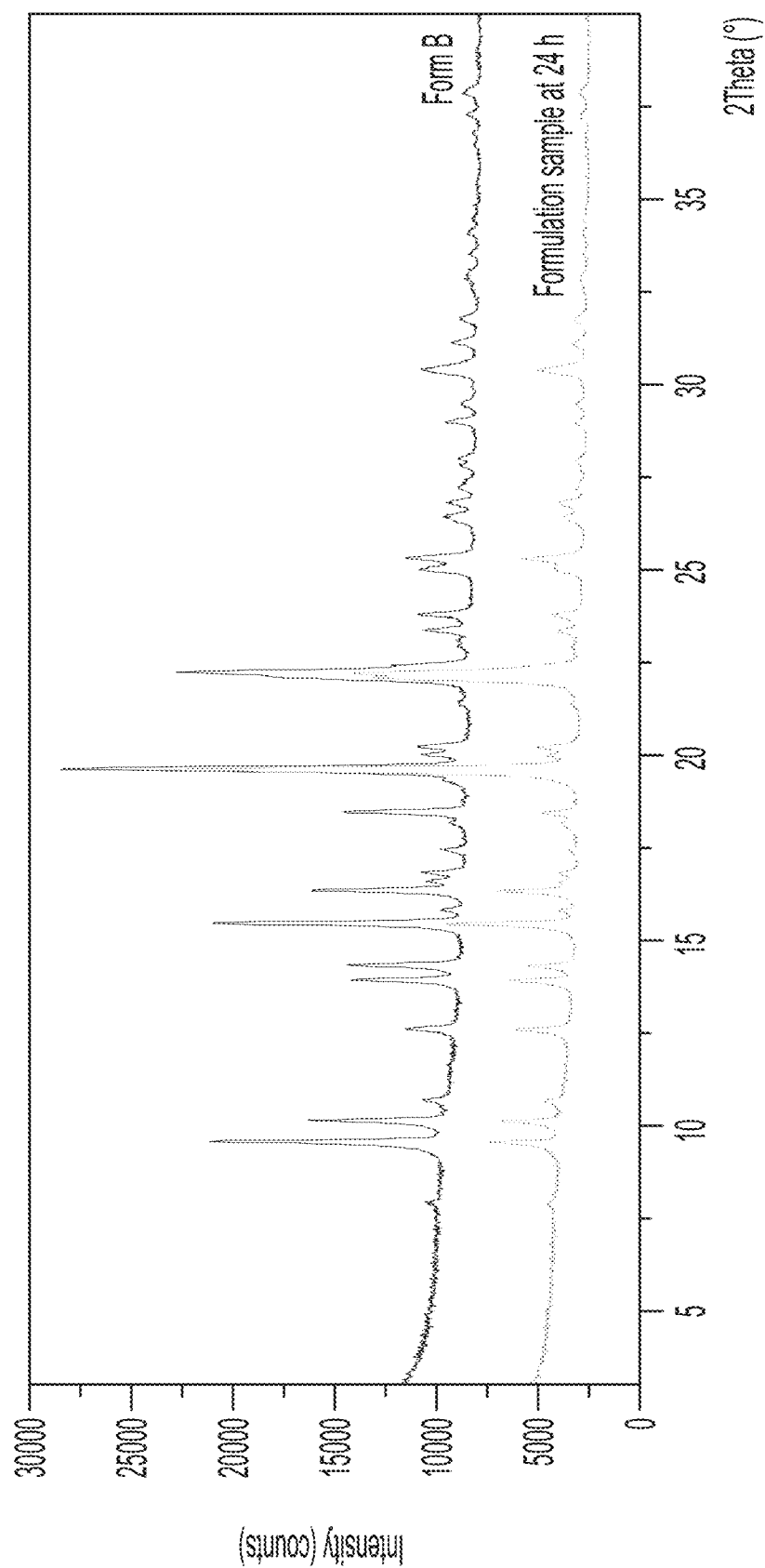
FIG. 15 depicts a series of XRPD patterns from the results of a phase stability evaluation of Compound 1 Form B.

Example 5—Evaluation of Phase Stability and Kinetic Solubility of Form B in a Formulation Kinetic solubility and phase stability of Form B was tested in a formulation (0.5% methyl cellulose (MC) and 0.5% Tween 80 in water). The sample was monitored by XRPD at 1, 2, 4 and 24 hours for phase stability. As shown in FIG. 15, no phase transformation was observed after 24 h. Kinetic solubility of Form B was measured in the same formulation at time points of 1, 2, 4 and 24 hour (Table 8). The supernatant was obtained by filtration and the concentration was measured by HPLC. The result showed that the solubility remained stable during 24 hours at RT. No significant degradation was observed from the solubility sample.

As summarized in Table 8 and FIG. 15, Form B showed 0.06 mg/mL solubility in 24 hours in the formulation, as well as no form change or significant degradation in the vehicle.

TABLE 8

| Time Point | Solubility (mg/mL) | Purity (% area at 240 nm) |
| --- | --- | --- |
| 1 h | 0.062 | 97.8 |
| 2 h | 0.062 | 97.8 |
| 4 h | 0.063 | 97.7 |
| 24 h | 0.060 | 97.7 |

Example 6—Formulations of Compound 1 Form B

Compound 1 Form B can be formulated into a form (e.g., a capsule or unit dosage form) for oral use.

Compound 1 Form B was incorporated into a unit dosage form by encapsulation in capsules comprising hydroxypropyl methylcellulose (HPMC). The composition of the capsule comprising HPMC was selected to provide suitable resistance to hydroscopic active compounds, with a suitable resistance to moisture permeation, not prone to moisture variability (e.g., about 13-16% moisture content in a hard gelatin capsule shell). The oral unit dosage form can be a capsule containing a dose strength of 0.3 mg, 3 mg, or 9 mg.

Compound 1 Form B was formulated into capsules containing 1% w/v of Compound 1 Form B with other excipients in a 1 mL shell vial, as summarized in Table 9.

TABLE 9

| Component | Function | Formulation 1 (rel. volume) | Formulation 2 (rel. volume) | Formulation 3 (rel. volume) |
| --- | --- | --- | --- | --- |
| Capryol 90 | Polymer | 0.5 | 0.5 | — |
| Capmul MCM | Polymer | 0.5 | — | 0.5 |
| PEG 4000 | Polymer | — | 0.5 | 0.5 |

Compound 1 Form B was formulated via dry blending into capsules in size 4 hard gelatin capsules as summarized in Table 10.

TABLE 10

| Component | Function | Formulation 4 (% w/w) | Formulation 5 (% w/w) | Formulation 6 (% w/w) |
| --- | --- | --- | --- | --- |
| Micronized Compound 1 Form B | Active | 11.25 | 11.25 | 11.25 |
| Parteck M100 (Mannitol) | Filler | 38.88 | 38.88 | 38.88 |
| Avicel PH 101 | Filler | 38.87 | 38.87 | 38.87 |
| Sodium dodecyl sulfate | Surfactant | 5.00 | — | — |
| Poloxamer 188 | Surfactant | — | 5.00 | — |
| Poloxamer 407 | Surfactant | — | — | 5.00 |
| Ac-Di-Sol | Disintegrant | 5.00 | 5.00 | 5.00 |
| Mg Stearate | Lubricant | 1.00 | 1.00 | 1.00 |

Equivalents

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A solid form of the free base of (4-(2-fluoro-4-(1-methyl-1H-benzo[d]imidazol-5-yl)benzoyl)piperazin-1-yl)(1-hydroxycyclopropyl)methanone designated the Form B solid form that exhibits a X-ray powder diffraction pattern (XRPD) (a) having characteristic peaks expressed in degrees 2-theta (±0.2 degrees 2-theta) at 9.6, 10.1, 15.4, 19.6, and 22.3 and (b) characterized by the absence of a characteristic peak expressed in degrees 2-theta (±0.2 degrees 2-theta) at 24.2.

2. The solid form of claim 1, wherein the solid form is characterized by a differential scanning calorimetry (DSC) thermogram having one endotherm at 225.7° C., when the DSC is performed at 10° C./min from about 20° C. to about 350° C. using dry nitrogen to purge the system.

3. The solid form of claim 1, wherein the solid form is characterized by the X-ray powder diffraction pattern shown in FIG. 3.

4. The solid form of claim 1, wherein the solid form is free of the Form C solid form of (4-(2-fluoro-4-(1-methyl-1H-benzo[d]imidazol-5-yl) benzoyl)piperazin-1-yl)(1-hydroxycyclopropyl)methanone.

5. The solid form of claim 1, wherein the solid form is free of the Form X solid form of (4-(2-fluoro-4-(1-methyl-1H-benzo[d]imidazol-5-yl)benzoyl) piperazin-1-yl)(1-hydroxycyclopropyl)methanone.

6. The solid form of claim 1, wherein the solid form is characterized by a mass change of less than about 0.5 wt % from 0% RH to 95% RH at 25 degrees C. by dynamic vapor sorption (DVS), when the DVS is performed according to Table 4

TABLE 4

| Parameters | Values |
| --- | --- |
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 360 min |
| Relative humidity (RH) range | 20% RH-95% RH-0% RH-95% RH |
| Relative humidity (RH) step size | 10%. |

7. The solid form of claim 1, wherein the solid form is characterized by a thermogravimetric analysis (TGA) weight loss of less than about 0.5% up to 100 degrees C., when the TGA is performed from 20-350 degrees C., at a ramp rate of 10 degrees C./min. and using dry nitrogen to purge the system.

8. The solid form of claim 1, wherein the solid form is characterized by a single endothermic peak onset temperature of about 223.9 degrees C. by differential scanning calorimetry (DSC) thermogram before decomposition, when the DSC is performed at 10° C./min from about 20° C. to about 350° C. using dry nitrogen to purge the system.

9. The solid form of claim 1, wherein the solid form exhibits an X-ray powder diffraction pattern (XRPD) having peaks expressed in degrees 2-theta at approximately:

| | | |
|---|---|---|
| 9.6 | 17.4 | 25.0 |
| 10.1 | 18.2 | 25.3 |
| 10.7 | 18.5 | 26.5 |
| 12.6 | 19.6 | 26.9 |
| 13.9 | 20.2 | 28.0 |
| 14.3 | 22.1 | |
| 15.4 | 22.3 | 29.0 |
| 16.4 | 23.4 | 29.5 |
| 16.6 | 23.8 | 30.5 |
| 31.1 | 32.9 | 37.3 |
| 31.8 | 34.1 | 37.9. |

10. The solid form of claim 1, wherein the solid form is characterized by an X-ray powder diffraction pattern (XRPD) having one or more peaks at substantially the same angles (2 theta±0.2), corresponding to d-spacing (angstroms±0.2) of:

| 2 Theta | d-spacing (Å) |
|---|---|
| 9.6 | 9.2 |
| 10.1 | 8.7 |
| 10.7 | 8.3 |
| 12.6 | 7.0 |
| 13.9 | 6.4 |
| 14.3 | 6.2 |
| 15.4 | 5.7 |
| 16.4 | 5.4 |
| 16.6 | 5.3 |
| 17.4 | 5.1 |
| 18.2 | 4.9 |
| 18.5 | 4.8 |
| 19.6 | 4.5 |
| 20.2 | 4.4 |
| 22.1 | 4.0 |
| 22.3 | 4.0 |
| 23.4 | 3.8 |
| 23.8 | 3.7 |
| 25.0 | 3.6 |
| 25.3 | 3.5 |
| 26.5 | 3.4 |
| 26.9 | 3.3 |
| 28.0 | 3.2 |
| 29.0 | 3.1 |
| 29.5 | 3.0 |
| 30.5 | 2.9 |
| 31.1 | 2.9 |
| 31.8 | 2.8 |
| 32.9 | 2.7 |
| 34.1 | 2.6 |
| 37.3 | 2.4 |
| 37.9 | 2.4. |

11. A pharmaceutical composition comprising the solid form of claim 1, and one or more pharmaceutically acceptable excipients.

12. The pharmaceutical composition of claim 11, wherein the pharmaceutical composition is formulated for oral administration.

13. A crystalline solid form of the free base of Compound 1,

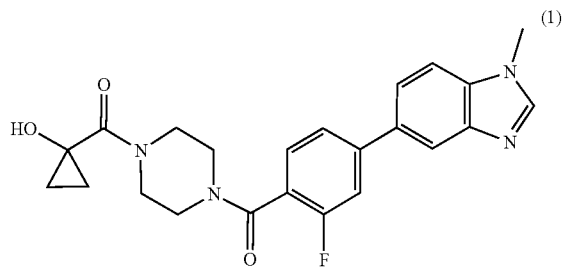 [SMILES: Cn1cnc2cc(-c3ccc(C(=O)N4CCN(C(=O)C5(O)CC5)CC4)c(F)c3)ccc21]

wherein the crystalline solid form exhibits an X-ray powder diffraction pattern (XRPD) (a) having characteristic peaks expressed in degrees 2-theta (±0.2) at 9.6, 10.1, 15.4, 19.6, and 22.3 and (b) characterized by the absence of a characteristic peak expressed in degrees 2-theta (±0.2 degrees 2-theta) at 24.2.

14. The solid form of claim 13, wherein the solid form is further characterized by one or more characteristics selected from the group consisting of:
 a. a thermogravimetric analysis (TGA) weight loss of less than about 0.5% up to 100 degrees C., when the TGA is performed from 20-350 degrees C., at a ramp rate of 10 degrees C./min. and using dry nitrogen to purge the system; and
 b. a single endothermic peak onset temperature of about 223.9 degrees C. and peak temperature of about 225.7 degrees C. by differential scanning calorimetry (DSC) before decomposition, when the DSC is performed at 10° C./min from about 20° C. to about 350° C. using dry nitrogen to purge the system; and
 c. a mass change of less than about 0.5 wt % from 0% RH to 95% RH at 25 degrees C. by dynamic vapor sorption (DVS), when the DVS is performed according to Table 4

TABLE 4

| Parameters | Values |
|---|---|
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 360 min |
| Relative humidity (RH) range | 20% RH-95% RH-0% RH-95% RH |
| Relative humidity (RH) step size | 10%. |

15. The solid form of claim 13, wherein the solid form is further characterized by:
 d. a thermogravimetric analysis (TGA) weight loss of less than about 0.5% up to 100 degrees C., when the TGA is performed from 20-350 degrees C., at a ramp rate of 10 degrees C./min. and using dry nitrogen to purge the system;
 e. a single endothermic peak onset temperature of about 223.9 degrees C. and peak temperature of about 225.7 degrees C. by differential scanning calorimetry (DSC) before decomposition, when the DSC is performed at 10° C./min from about 20° C. to about 350° C. using dry nitrogen to purge the system; and
 f. a mass change of less than about 0.5 wt % from 0% RH to 95% RH at 25 degrees C. by dynamic vapor sorption (DVS) when the DVS is performed according to Table 4

TABLE 4

| Parameters | Values |
|---|---|
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 360 min |
| Relative humidity (RH) range | 20% RH-95% RH-0% RH-95% RH |
| Relative humidity (RH) step size | 10%. |

16. A pharmaceutical composition formulated for oral administration, the composition comprising the solid form of claim 13, and one or more pharmaceutically acceptable excipients.

17. A pharmaceutical composition comprising a solid form of the free base of Compound 1 and one or more pharmaceutically acceptable excipients,

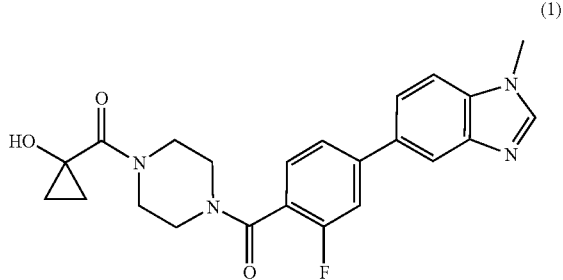 [SMILES: Cn1cnc2cc(-c3ccc(C(=O)N4CCN(C(=O)C5(O)CC5)CC4)c(F)c3)ccc21]

(1)

wherein the solid form of Compound 1 exhibits a X-ray powder diffraction pattern (XRPD) having characteristic peaks expressed in degrees 2-theta (±0.2 degrees 2-theta) at 9.6, 10.1, 15.4, 19.6, and 22.3.

18. The pharmaceutical composition of claim 17, wherein the solid form is further characterized by one or more characteristics selected from the group consisting of:
   g. a single endothermic peak onset temperature of about 223.9 degrees C. by differential scanning calorimetry (DSC) thermogram before decomposition, when the DSC is performed at 10° C./min from about 20° C. to about 350° C. using dry nitrogen to purge the system;
   h. a differential scanning calorimetry (DSC) thermogram having a single endotherm at a peak temperature of about 225.7 degrees C., when the DSC is performed at 10° C./min from about 20° C. to about 350° C. using dry nitrogen to purge the system;
   i. a thermogravimetric analysis (TGA) weight loss of less than about 0.5% up to 100 degrees C., when the TGA is performed from 20-350 degrees C., at a ramp rate of 10 degrees C./min. and using dry nitrogen to purge the system; and
   j. a mass change of less than about 0.5 wt % from 0% RH to 95% RH at 25 degrees C. by dynamic vapor sorption (DVS) when the DVS is performed according to Table 4

TABLE 4

| Parameters | Values |
|---|---|
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 360 min |
| Relative humidity (RH) range | 20% RH-95% RH-0% RH-95% RH |
| Relative humidity (RH) step size | 10%. |

19. The pharmaceutical composition of claim 17, wherein the solid form is further characterized by:
   k. a single endothermic peak onset temperature of about 223.9 degrees C. and peak temperature of about 225.7 degrees C. by differential scanning calorimetry (DSC) before decomposition, when the DSC is performed at 10° C./min from about 20° C. to about 350° C. using dry nitrogen to purge the system;
   l. a thermogravimetric analysis (TGA) weight loss of less than about 0.5% up to 100 degrees C., when the TGA is performed from 20-350 degrees C., at a ramp rate of 10 degrees C./min. and using dry nitrogen to purge the system; and
   m. a mass change of less than about 0.5 wt % from 0% RH to 95% RH at 25 degrees C. by dynamic vapor sorption (DVS) when the DVS is performed according to Table 4

TABLE 4

| Parameters | Values |
|---|---|
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 360 min |
| Relative humidity (RH) range | 20% RH-95% RH-0% RH-95% RH |
| Relative humidity (RH) step size | 10%. |

20. The pharmaceutical composition of claim 19, wherein the pharmaceutical composition is formulated for oral administration.

21. The pharmaceutical composition of claim 17, wherein the pharmaceutical composition is prepared as an oral unit dosage form.

22. The pharmaceutical composition of claim 17, wherein the solid form exhibits an X-ray powder diffraction pattern (XRPD) having peaks expressed in degrees 2-theta at approximately:

| | | |
|---|---|---|
| 9.6 | 17.4 | 25.0 |
| 10.1 | 18.2 | 25.3 |
| 10.7 | 18.5 | 26.5 |
| 12.6 | 19.6 | 26.9 |
| 13.9 | 20.2 | 28.0 |
| 14.3 | 22.1 | |
| 15.4 | 22.3 | 29.0 |
| 16.4 | 23.4 | 29.5 |
| 16.6 | 23.8 | 30.5 |
| 31.1 | 32.9 | 37.3 |
| 31.8 | 34.1 | 37.9. |

23. The pharmaceutical composition of claim 17, wherein the solid form is characterized by a X-ray powder diffraction pattern (XRPD) having one or more peaks at substantially the same angles (2 theta±0.2), corresponding to d-spacing (angstroms±0.2) of:

| 2 Theta | d-spacing (Å) |
|---|---|
| 9.6 | 9.2 |
| 10.1 | 8.7 |
| 10.7 | 8.3 |
| 12.6 | 7.0 |
| 13.9 | 6.4 |
| 14.3 | 6.2 |
| 15.4 | 5.7 |
| 16.4 | 5.4 |
| 16.6 | 5.3 |
| 17.4 | 5.1 |
| 18.2 | 4.9 |
| 18.5 | 4.8 |
| 19.6 | 4.5 |
| 20.2 | 4.4 |
| 22.1 | 4.0 |
| 22.3 | 4.0 |
| 23.4 | 3.8 |
| 23.8 | 3.7 |
| 25.0 | 3.6 |
| 25.3 | 3.5 |
| 26.5 | 3.4 |
| 26.9 | 3.3 |
| 28.0 | 3.2 |
| 29.0 | 3.1 |
| 29.5 | 3.0 |
| 30.5 | 2.9 |
| 31.1 | 2.9 |
| 31.8 | 2.8 |
| 32.9 | 2.7 |
| 34.1 | 2.6 |
| 37.3 | 2.4 |
| 37.9 | 2.4. |

\* \* \* \* \*